US012663345B2

(12) United States Patent
Fontanez et al.

(10) Patent No.: US 12,663,345 B2
(45) Date of Patent: Jun. 23, 2026

(54) DEVICES FOR GENERATING MONODISPERSE DROPLETS FROM A BULK LIQUID

(71) Applicant: ILLUMINA, INC., San Diego, CA (US)

(72) Inventors: Kristina Fontanez, Arlington, MA (US); Robert Meltzer, Belmont, MA (US); Yi Xue, Shrewsbury, MA (US); Sepehr Kiani, Watertown, MA (US)

(73) Assignee: Illumina, Inc., San Diego, CA (US)

( * ) Notice: Subject to any disclaimer, the term of this patent is extended or adjusted under 35 U.S.C. 154(b) by 652 days.

(21) Appl. No.: 17/146,768

(22) Filed: Jan. 12, 2021

(65) Prior Publication Data

US 2021/0215591 A1     Jul. 15, 2021

Related U.S. Application Data

(60) Provisional application No. 62/960,251, filed on Jan. 13, 2020.

(51) Int. Cl.
| | |
|---|---|
| *G01N 1/38* | (2006.01) |
| *A61B 10/00* | (2006.01) |
| *B01F 25/10* | (2022.01) |
| *B01F 101/23* | (2022.01) |
| *G01N 1/40* | (2006.01) |
(Continued)

(52) U.S. Cl.
CPC .............. *G01N 1/38* (2013.01); *B01F 25/10* (2022.01); *G01N 1/4077* (2013.01); *G01N*

*15/1023* (2024.01); *A61B 10/0096* (2013.01); *B01F 2101/23* (2022.01); *G01N 2015/0053* (2013.01);
(Continued)

(58) Field of Classification Search
CPC ............. G01N 15/1056; G01N 1/4077; G01N 2015/0053; G01N 2015/0065; G01N 2015/1006; G01N 15/1456; G01N 15/1434; G01N 35/026; G01N 2015/003; G01N 1/38; G01N 2015/1481;
(Continued)

(56) References Cited

U.S. PATENT DOCUMENTS

| | | | |
|---|---|---|---|
| 4,202,634 A | 5/1980 | Kraft et al. | |
| 4,305,668 A | 12/1981 | Bilbrey | |
(Continued)

FOREIGN PATENT DOCUMENTS

| | | |
|---|---|---|
| AU | 2013203624 A1 | 5/2013 |
| CN | 112410213 A | 2/2021 |
(Continued)

OTHER PUBLICATIONS

Hatori, 2019, Particle-Templated Emulsification for Microfluidics-Free Digital Biology, Analytical Chemistry, 90:9813-9820.
(Continued)

*Primary Examiner* — Marrit Eyassu
(74) *Attorney, Agent, or Firm* — Illumina, Inc.

(57) ABSTRACT

The invention provides devices that generate monodisperse droplets from a bulk liquid. The devices include a shearing mechanism, a holder for a vessel containing a liquid, and an optical system that transmit light to, and detects light from, liquid in the vessel. The invention also provides methods of using such devices to produce monodisperse droplets.

17 Claims, 16 Drawing Sheets

(51) Int. Cl.

| | |
|---|---|
| *G01N 15/00* | (2024.01) |
| *G01N 15/01* | (2024.01) |
| *G01N 15/10* | (2024.01) |
| *G01N 15/14* | (2024.01) |

(52) U.S. Cl.
CPC ..... *G01N 15/01* (2024.01); *G01N 2015/1006* (2013.01); *G01N 2015/1481* (2013.01)

(58) Field of Classification Search
CPC ........... G01N 2035/00524; B01F 25/10; B01F 2101/23; B01F 23/4111; B01F 35/2144; A61B 10/0096
USPC ........................................................ 73/61.72
See application file for complete search history.

(56) References Cited

U.S. PATENT DOCUMENTS

| | | | |
|---|---|---|---|
| 4,553,955 A | | 11/1985 | Lam et al. |
| 4,701,415 A | | 10/1987 | Dutton |
| 4,883,644 A | | 11/1989 | Perlman |
| 5,036,989 A | | 8/1991 | Carilli |
| 5,512,439 A | | 4/1996 | Hornes et al. |
| 5,632,388 A | | 5/1997 | Morrison et al. |
| 5,813,759 A | | 9/1998 | Gebrian |
| 6,186,657 B1 | * | 2/2001 | Fuchsbichler .......... B01F 23/50 |
| | | | 366/173.2 |
| 6,210,891 B1 | | 4/2001 | Nyren et al. |
| 6,306,597 B1 | | 10/2001 | Macevicz |
| 6,309,833 B1 | | 10/2001 | Edman et al. |
| 6,828,100 B1 | | 12/2004 | Ronaghi |
| 6,833,246 B2 | | 12/2004 | Balasubramanian |
| 6,911,345 B2 | | 6/2005 | Quake et al. |
| 7,232,656 B2 | | 6/2007 | Balasubramanian et al. |
| 7,296,924 B2 | | 11/2007 | Czarnek |
| 7,339,671 B2 | | 3/2008 | Peng |
| 7,361,472 B2 | * | 4/2008 | Yguerabide ......... C12Q 1/6816 |
| | | | 435/7.1 |
| 7,537,897 B2 | | 5/2009 | Brenner et al. |
| 7,598,035 B2 | | 10/2009 | Macevicz |
| 7,835,871 B2 | | 11/2010 | Kain et al. |
| 7,842,457 B2 | | 11/2010 | Berka et al. |
| 7,960,120 B2 | | 6/2011 | Rigatti et al. |
| 8,012,690 B2 | | 9/2011 | Berka et al. |
| 8,629,323 B2 | | 1/2014 | Weeks |
| 8,715,934 B2 | | 5/2014 | Diehl et al. |
| 8,748,102 B2 | | 6/2014 | Berka et al. |
| 8,765,380 B2 | | 7/2014 | Berka et al. |
| 9,011,777 B2 | | 4/2015 | Beer |
| 9,012,390 B2 | | 4/2015 | Holtze et al. |
| 9,085,798 B2 | | 7/2015 | Chee |
| 9,260,751 B2 | | 2/2016 | Diehl et al. |
| 9,388,465 B2 | | 7/2016 | Hindson et al. |
| 9,399,797 B2 | | 7/2016 | Hutchison et al. |
| 9,562,837 B2 | * | 2/2017 | Link .................... C12Q 1/6806 |
| 9,567,645 B2 | | 2/2017 | Fan et al. |
| 9,567,646 B2 | | 2/2017 | Fan et al. |
| 9,580,736 B2 | | 2/2017 | Tan et al. |
| 9,598,736 B2 | | 3/2017 | Fan et al. |
| 9,637,799 B2 | | 5/2017 | Fan et al. |
| 9,650,629 B2 | | 5/2017 | Froehlich et al. |
| 9,695,392 B2 | | 7/2017 | Sherman et al. |
| 9,695,474 B2 | | 7/2017 | Johnson et al. |
| 9,701,998 B2 | | 7/2017 | Hindson et al. |
| 9,708,654 B2 | | 7/2017 | Hunicke-Smith et al. |
| 9,783,847 B2 | | 10/2017 | Chee |
| 9,951,386 B2 | | 4/2018 | Hindson et al. |
| 10,030,267 B2 | | 7/2018 | Hindson et al. |
| 10,041,116 B2 | | 8/2018 | Hindson et al. |
| 10,131,958 B1 | | 11/2018 | Fan et al. |
| 10,151,003 B2 | | 12/2018 | Fan et al. |
| 10,155,981 B2 | | 12/2018 | Brenner et al. |
| 10,202,628 B2 | | 2/2019 | Church et al. |
| 10,208,356 B1 | | 2/2019 | Fan et al. |

| | | | |
|---|---|---|---|
| 10,221,442 B2 | | 3/2019 | Hindson et al. |
| 10,240,192 B2 | | 3/2019 | Berka et al. |
| 10,240,197 B1 | | 3/2019 | Brenner et al. |
| 10,253,375 B1 | | 4/2019 | Fan et al. |
| 10,266,883 B2 | | 4/2019 | Chee |
| 10,280,459 B1 | | 5/2019 | Brenner et al. |
| 10,285,940 B2 | | 5/2019 | Mason et al. |
| 10,329,557 B2 | | 6/2019 | Johnson et al. |
| 10,344,329 B2 | | 7/2019 | Hindson et al. |
| 10,392,662 B1 | | 8/2019 | Brenner et al. |
| 10,400,280 B2 | | 9/2019 | Hindson et al. |
| 10,415,030 B2 | | 9/2019 | Marshall et al. |
| 10,457,986 B2 | | 10/2019 | Hindson et al. |
| 10,501,793 B2 | | 12/2019 | Chee |
| 10,533,950 B2 | | 1/2020 | Herzog et al. |
| 10,584,381 B2 | | 3/2020 | Hindson et al. |
| 10,739,236 B1 | | 8/2020 | Hopkins |
| 11,008,607 B2 | | 5/2021 | Chee |
| 11,060,149 B2 | | 7/2021 | Steelman |
| 11,104,961 B2 | | 8/2021 | Fontanez et al. |
| 11,142,791 B2 | | 10/2021 | Abate et al. |
| 11,549,138 B2 | | 1/2023 | Chee |
| 11,692,214 B2 | | 7/2023 | Nolan |
| 11,932,902 B2 | | 3/2024 | Nolan |
| 12,234,505 B2 | | 2/2025 | Chee |
| 12,275,993 B2 | | 4/2025 | Ziraldo et al. |
| 12,297,487 B2 | | 5/2025 | Chee |
| 12,305,239 B2 | | 5/2025 | Ziraldo et al. |
| 12,416,102 B2 | | 9/2025 | Ziraldo et al. |
| 2002/0132251 A1 | | 9/2002 | Shuber |
| 2003/0143599 A1 | | 7/2003 | Makarov et al. |
| 2003/0180737 A1 | | 9/2003 | Gu et al. |
| 2004/0005585 A1 | | 1/2004 | Bi et al. |
| 2005/0051466 A1 | * | 3/2005 | Carter .................... G01N 15/05 |
| | | | 210/512.1 |
| 2006/0024681 A1 | | 2/2006 | Smith et al. |
| 2006/0177836 A1 | | 8/2006 | McKeman et al. |
| 2006/0177936 A1 | | 8/2006 | Shneider et al. |
| 2006/0292611 A1 | | 12/2006 | Berka et al. |
| 2007/0080316 A1 | | 4/2007 | Sauer et al. |
| 2007/0114362 A1 | | 5/2007 | Feng et al. |
| 2008/0004436 A1 | | 1/2008 | Tawfik |
| 2008/0056059 A1 | | 3/2008 | Manera et al. |
| 2009/0238727 A1 | | 9/2009 | Sinclair et al. |
| 2009/0280475 A1 | | 11/2009 | Pollack et al. |
| 2011/0009278 A1 | | 1/2011 | Kain et al. |
| 2011/0086780 A1 | | 4/2011 | Colston, Jr. et al. |
| 2011/0118151 A1 | | 5/2011 | Eshoo et al. |
| 2011/0176976 A1 | * | 7/2011 | Ebi ........................ G01N 35/04 |
| | | | 422/547 |
| 2011/0311978 A1 | | 12/2011 | Makarewicz, Jr. et al. |
| 2012/0180941 A1 | | 7/2012 | Piramoon et al. |
| 2012/0295269 A1 | | 11/2012 | Pourahmadi et al. |
| 2012/0316074 A1 | | 12/2012 | Saxonov |
| 2013/0115169 A1 | | 5/2013 | Lahann et al. |
| 2014/0024020 A1 | * | 1/2014 | Tanabe .................. G02B 21/16 |
| | | | 435/5 |
| 2014/0155295 A1 | | 6/2014 | Hindson et al. |
| 2014/0293735 A1 | | 10/2014 | Vidakovic et al. |
| 2014/0309795 A1 | * | 10/2014 | Norton .............. G01N 15/1459 |
| | | | 700/282 |
| 2015/0133312 A1 | | 5/2015 | Bielas et al. |
| 2015/0225777 A1 | | 8/2015 | Hindson et al. |
| 2015/0232942 A1 | * | 8/2015 | Abate .................. C12Q 1/6844 |
| | | | 435/6.12 |
| 2016/0121325 A1 | | 5/2016 | Masquelier et al. |
| 2016/0186267 A1 | | 6/2016 | So et al. |
| 2016/0250608 A1 | | 9/2016 | Anders et al. |
| 2016/0266015 A1 | * | 9/2016 | Loo .................. G01N 35/00722 |
| 2016/0274103 A1 | | 9/2016 | Piloto et al. |
| 2017/0073280 A1 | | 3/2017 | Jones |
| 2017/0153248 A1 | * | 6/2017 | Goix .................. G01N 15/1459 |
| 2017/0165670 A1 | | 6/2017 | Harder et al. |
| 2017/0189909 A1 | * | 7/2017 | Lee ........................ C12N 11/04 |
| 2017/0192030 A1 | | 7/2017 | Lapham et al. |
| 2017/0218437 A1 | | 8/2017 | Seul et al. |
| 2017/0232417 A1 | | 8/2017 | Lebofsky et al. |
| 2017/0255160 A1 | | 9/2017 | Numata et al. |
| 2017/0269112 A1 | | 9/2017 | Gerstel |

(56) References Cited

U.S. PATENT DOCUMENTS

| | | | |
|---|---|---|---|
| 2018/0010105 A1 | 1/2018 | Rogers et al. | |
| 2018/0051321 A1 | 2/2018 | Hindson et al. | |
| 2018/0119216 A1 | 5/2018 | Jamshidi et al. | |
| 2018/0133715 A1 | 5/2018 | Craig et al. | |
| 2018/0179553 A1 | 6/2018 | Watson et al. | |
| 2018/0216162 A1 | 8/2018 | Belhocine et al. | |
| 2018/0237836 A1 | 8/2018 | Abate et al. | |
| 2018/0274027 A1 | 9/2018 | Hindson et al. | |
| 2018/0340880 A1* | 11/2018 | Matsumoto | B05C 5/00 |
| 2018/0355407 A1 | 12/2018 | Utharala et al. | |
| 2019/0030539 A1* | 1/2019 | Vermaas | B01D 69/02 |
| 2019/0039034 A1 | 2/2019 | Siow et al. | |
| 2019/0085412 A1 | 3/2019 | Fan et al. | |
| 2019/0153532 A1 | 5/2019 | Bharadwaj et al. | |
| 2019/0153550 A1 | 5/2019 | Steinmetzer et al. | |
| 2019/0177789 A1 | 6/2019 | Hindson et al. | |
| 2019/0323003 A1 | 10/2019 | Ramji et al. | |
| 2019/0323091 A1 | 10/2019 | Bramlett et al. | |
| 2019/0352714 A1 | 11/2019 | Salk et al. | |
| 2019/0381497 A1 | 12/2019 | Di Carlo et al. | |
| 2019/0382753 A1 | 12/2019 | Steemers et al. | |
| 2020/0040385 A1 | 2/2020 | Beechem et al. | |
| 2020/0061618 A1 | 2/2020 | Lee et al. | |
| 2020/0080112 A1 | 3/2020 | Zhang et al. | |
| 2020/0190513 A1 | 6/2020 | Fernandez et al. | |
| 2020/0261879 A1* | 8/2020 | Abate | A61K 9/107 |
| 2020/0324287 A1 | 10/2020 | Vijayan et al. | |
| 2020/0376488 A1 | 12/2020 | Wu et al. | |
| 2021/0010070 A1 | 1/2021 | Schnall-Levin et al. | |
| 2021/0054369 A1 | 2/2021 | Meltzer et al. | |
| 2021/0214721 A1 | 7/2021 | Fontanez et al. | |
| 2021/0214763 A1 | 7/2021 | Fontanez et al. | |
| 2021/0214769 A1 | 7/2021 | Fontanez et al. | |
| 2021/0214792 A1 | 7/2021 | Fontanez et al. | |
| 2021/0214802 A1 | 7/2021 | Fontanez et al. | |
| 2021/0215591 A1 | 7/2021 | Fontanez et al. | |
| 2021/0291185 A1 | 9/2021 | Lee et al. | |
| 2021/0301354 A1 | 9/2021 | Kiani | |
| 2021/0308691 A1 | 10/2021 | Horak | |
| 2021/0332432 A1 | 10/2021 | Kiani | |
| 2021/0340596 A1 | 11/2021 | Meltzer et al. | |
| 2021/0381064 A1 | 12/2021 | Fontanez et al. | |
| 2022/0017892 A1 | 1/2022 | Meltzer et al. | |
| 2022/0135966 A1 | 5/2022 | Meltzer | |
| 2022/0136071 A1 | 5/2022 | Meltzer | |
| 2022/0143615 A1 | 5/2022 | Medoro | |
| 2022/0154248 A1 | 5/2022 | Abate et al. | |
| 2022/0234043 A1 | 7/2022 | Tanabe et al. | |
| 2022/0235416 A1 | 7/2022 | Fontanez et al. | |
| 2022/0267761 A1 | 8/2022 | Fontanez et al. | |

FOREIGN PATENT DOCUMENTS

| | | | |
|---|---|---|---|
| CN | 113274927 A | 8/2021 | |
| EP | 1441225 A1 | 7/2004 | |
| EP | 1767275 A1 | 3/2007 | |
| EP | 1839756 A1 | 10/2007 | |
| EP | 1877170 B1 | 6/2010 | |
| EP | 3819637 A1 | 5/2021 | |
| JP | 2003080115 A | 3/2003 | |
| JP | 2021072863 A | 5/2021 | |
| WO | 1997/008547 A1 | 3/1997 | |
| WO | WO-2009114619 A1 * | 9/2009 | G01N 11/142 |
| WO | 2010/117620 A2 | 10/2010 | |
| WO | 2011/047307 A1 | 4/2011 | |
| WO | WO-2011156084 A1 | 12/2011 | |
| WO | 2012/116146 A1 | 8/2012 | |
| WO | 2012/149042 A2 | 11/2012 | |
| WO | 2013/165748 A1 | 11/2013 | |
| WO | 2014/028537 A1 | 2/2014 | |
| WO | 2014/100434 A1 | 6/2014 | |
| WO | 2014/146025 A1 | 9/2014 | |
| WO | 2014/153071 A1 | 9/2014 | |
| WO | 2015/157369 A1 | 10/2015 | |
| WO | 2015/187792 A1 | 12/2015 | |
| WO | 2016/025815 A1 | 2/2016 | |
| WO | 2016/040476 A1 | 3/2016 | |
| WO | 2016/126871 A2 | 8/2016 | |
| WO | 2016/138080 A1 | 9/2016 | |
| WO | 2016/172373 A1 | 10/2016 | |
| WO | 2017/161306 A1 | 9/2017 | |
| WO | WO-2017201451 A1 * | 11/2017 | G01F 1/704 |
| WO | 2019/011971 A1 | 1/2019 | |
| WO | 2019/023627 A1 | 1/2019 | |
| WO | WO-2019050840 A1 | 3/2019 | |
| WO | 2019/139650 A2 | 7/2019 | |
| WO | 2019/157529 A1 | 8/2019 | |
| WO | 2019/204229 A1 | 10/2019 | |
| WO | 2019/217552 A1 | 11/2019 | |
| WO | 2019/222523 A2 | 11/2019 | |
| WO | 20200037214 A1 | 2/2020 | |
| WO | 2020/069268 A1 | 4/2020 | |
| WO | 2020/069298 A1 | 4/2020 | |
| WO | WO-2020156879 A1 | 8/2020 | |

OTHER PUBLICATIONS

International Search Report and Written Opinion issued in International Application No. PCT/US2020/47214, date of mailing: Feb. 2, 2021, 14 pages.

International Search Report and Written Opinion issued in International Application No. PCT/US2021/013042, date of mailing: Mar. 29, 2021, 9 pages.

International Search Report and Written Opinion issued in International Application No. PCT/US2021/013045, date of mailing: Mar. 29, 2021, 8 pages.

International Search Report and Written Opinion issued in International Application No. PCT/US2021/013065, date of mailing: Mar. 29, 2021, 11 pages.

International Search Report and Written Opinion issued in International Application No. PCT/US2021/013066, date of mailing: Mar. 29, 2021, 11 pages.

International Search Report and Written Opinion issued in International Application No. PCT/US2021/13048, date of mailing: Mar. 31, 2021, 20 pages.

International Search Report and Written Opinion issued in International Application No. PCT/US2021/13069, date of mailing: Apr. 1, 2021, 14 pages.

Kumari, 2017, Quantification of Circulating Free DNA as a Diagnostic Marker in Gall Bladder Cancer, Pathology & Oncology Research, 23:91-97.

Mazutis, 2013, Singl-cell analysis and sorting using droplet-based microfluidics, Nature Protocols, 8(5):870-891.

Non-Final Office Action issued in U.S. Appl. No. 17/146,986, date of mailing: Mar. 11, 2021, 7 pages.

Strachan, Human Molecular Genetics 2 (Wiley-Liss, New York, 1999).

Vitale, 2019, An Optimized Workflow to Evaluate Estrogen Receptor Gene Mutations in Small Amounts of Cell-Fee DNA, The Journal of Molecular Diagnostics, 21(1):123-127.

Berensmeier, 2006, Magnetic particles for the separation and purification of necleic acids, Applied Microbiology and Biotechnology, 73:495-504.

Biocompare, 2013, How to maintain a constant temp in your CO2 incubator, Jan. 17, 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.

Brouzes, 2009, Droplet microfluidic technology for single-cell high-throughput screening, Proc Natl Acad Sci 106 (34):14195-14200.

Cai, 2019, Selection of DNA-encoded libraries to protein targets within and on living cells, Journal of the American Chemical Society, 141(43):1-11.

Cheng, 2020, Ultra-senstive and rapid detection of nucleic acids and microorganisms in body fluids using single molecule tethering, Nature Communications, 11(1):1-9.

Datlinger, 2017, Pooled CRISPR screening with single-cell transcriptome readout, Nature Methods 4(3):297-301.

(56) References Cited

OTHER PUBLICATIONS

High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page.

Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.

Kim, 2018, Single-Cell RT-PCR in Microfluidic Droplets with Integrated Chemical Lysis, Anal Chem 90(2):1273-1279.

Klein, 2015, Droplet barcoding for single cell transcriptomics applied to embryonic stem cells, Cells, 161(5):1187-1201.

Kukurba, 2015, RNA Sequencing and Analysis, Cold Spring Harb Protoc 11:951-969.

Markus, 2021, Analysis of recurrently protected genomic regions in cell-free DNA found in urine, Science Translational Medicine, 13(581):1-31.

Patel, 2019, Design and fabrication of low cost vortex mixer using additive manufacturing, International Journal of Applied Engineering Research 14(1):246-249.

Petersen, 2021, Screening of DNA-encoded small molecule libraries inside a living cell, Journal of the American Chemical Society, 143(7):2751-2756.

Quail, 2012, A tale of three next generation sequencing platforms: comparison of Ion Torrent, Pacific Biosciences and Illumina MiSeq sequencers, BMC Genomics 13:341, 13 pages.

Replogle, 2020, Combinatorial single-cell CRISPR screens by direct guide RNA capture and targeted sequencing, Nat. Biotechnol. 38(8):954-961.

Stoeckius, 2017, Large-scale simultaneous measurements of epitopes and transcriptomes in single cells, Nat Methods 14(9):865-868.

Tokunaga, 2013, Systematic exploration of lipophilic tags that allow efficient anchoring of aptamers to live cell surfaces, Chem Lett 42(2):127-129.

Bowman, 2013, Multiplexed Illumina sequencing libraries from picogram quantities of DNA, BMC Genomics 14:466 (8 pages).

Eastbum, 2013, Ultrahigh-trhoughput mammalian single-cell reverse-transcriptase polymerase chain reaction in microfluidic drops, Anal Chem 85:8016-8021.

Figueiredo, 2007, Cost effective method for construction of high quality cDNA libraries, Biomol Eng 24:419-421.

Fu, 2015, Uniform and accurate single-cell sequencing based on emulsion whole-genome amplification, PNAS 112 (38):11923-11928.

Int Search Report and Written Op mailed Jun. 30, 2021, for Int Application No. PCT/US2021/023815, filed Mar. 24, 2021 (14 pages).

International Search Report issued in International Application No. PCT/US2021/022503, date of mailing: Aug. 11, 2021, 9 pages.

Kumaresan, 2008, High-throughput single copy DNA amplification and cell analysis in engineered nanoliter droplets, Anal Chem, 80:3522-3529.

Lage, 2003, Whole genome analysis of genetic alterations in small DNA samples using hyperbranched strand displacement amplification and array-CGH, Genome Res 13:294-307.

Lyons, 2017, Large-scale DNA barcode library generation for biomolecule identification in high-throughput screens, Sci Rep 7:13899 (7 pages).

Nishikawa, 2015, Monodisperse picoliter droplets for low-bias and contamination-free reactions in single-cell whole genome amplification, PLoSOne 10(9):e0138733 (15 pages).

Roche, 2011, emPCR amplificaiotn method manual, 454 Life Sciences Corp (12 pages).

Sidore, 2016, Enhanced sequencing coverage with digital droplet multiple displacement amplification, Nucl Acids Res 44(7):e66 (9 pages).

Stoeckius, 2017, Simultaneous epitope and transcriptome measurment in single cells, Nat Meth online pub (10 pages).

Tamminen, 2015, Single gene-based distinction of individual microbial genomes from a mixed population of microbial cells Front Microb 6:195 (10 pages).

Walls, 2020, Structure, Function, and Antigenicity of the SARS-CoV-2 Spike Glcoprotein, Cell, 181(2):281-292.

Zilionis, 2016, Single-cell barcoding and sequencing using droplet microfluidics, Natutre Prot 12(1):44-73.

Fan J., "Barcode Doublets", JEFWorks Lab, 2017, pp. 1-5.

International Patent Application No. PCT/US2022/037078, filed Jul. 14, 2022, International Search Report and Written Opinion issued Oct. 12, 2022, 21 pages.

International Patent Application No. PCT/US2022/037129, filed Jul. 14, 2022, International Search Report and Written Opinion issued Oct. 11, 2022, 16 Pages.

International Search Report and Written Opinion for International Application No. PCT/US2022/048785, Mar. 17, 2023, 9 pages.

Karlsson K., "Counting Molecules in Cell-free DNA and Single Cells RNA", Thesis, Division of Molecular Neurobiology Department of Medical Biochemistry and Biophysics, Karolinska Institutet, 2016, 52 Pages.

Suh S.K., et al., "Synthesis of Magnetic Hydrogel Microparticles for Bioassays and Tweezer Manipulation in Microwells", Microfluid ganofluid, vol. 13, 2012, pp. 655-674.

Kumari S., et al., "Quantification of Circulating Free DNA as a Diagnostic Marker in Gall Bladder Cancer", Cancer, Pathology & Oncology Research, Jan. 2017, vol. 23, No. 1, pp. 91-97.

Quail M.A., et al., "A Tale of Three Next Generation Sequencing Platforms: Comparison of Ion Torrent, Pacific Biosciences and Ilumina MiSeq Sequencers", BMC Genomics, vol. 13, No. 341, Jul. 24, 2012, pp. 1-13.

* cited by examiner

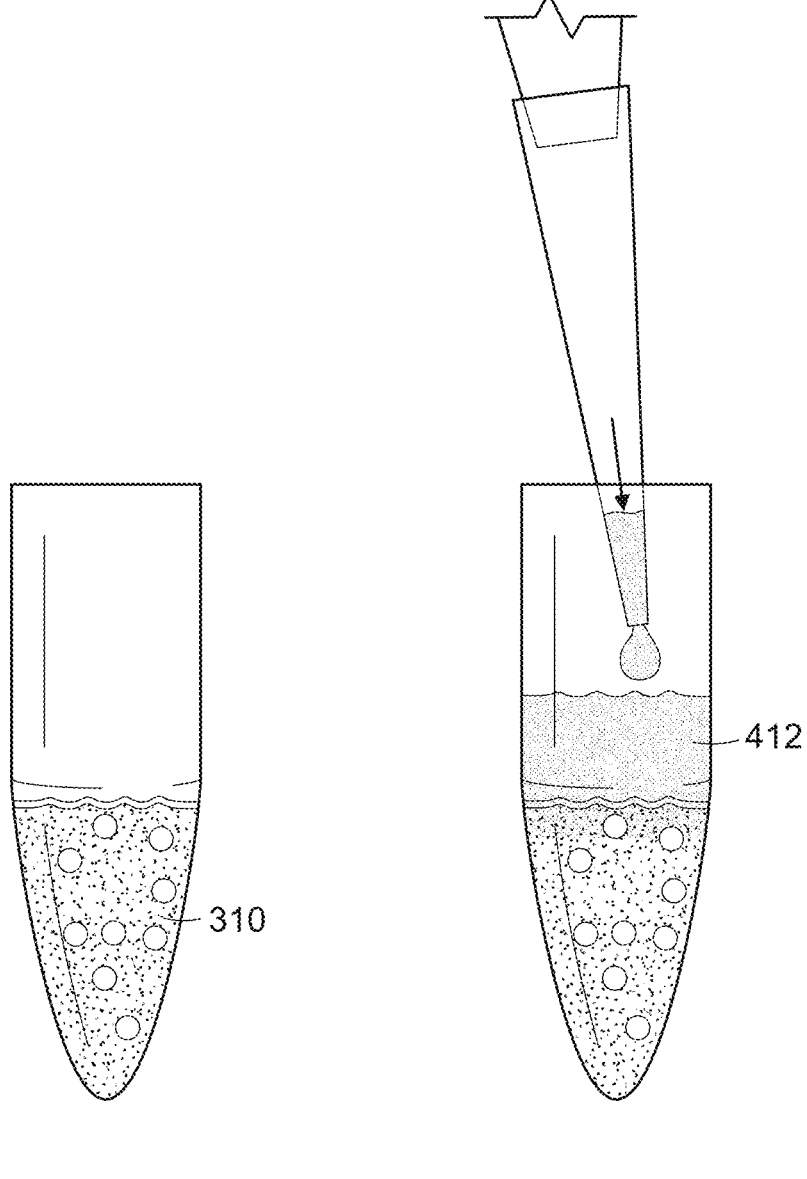
FIG. 3                    FIG. 4

1830

1832

DEVICES FOR GENERATING MONODISPERSE DROPLETS FROM A BULK LIQUID

FIELD OF THE INVENTION

The invention relates generally to devices for medical, diagnostic, and biological research applications and the use of such devices.

BACKGROUND

A major barrier to successful treatment of many types of cancer is the inability to detect the disease in an early stage. Cancers result from changes in gene expression in individual cells, and such changes allow the cells to proliferate, invade other tissues, and hijack the body's resources. In early stages, however, the genetically altered cells represent a tiny fraction of the cells in a particular tissue or population. Consequently, the stage in which cells harboring deleterious mutations can be most easily eradicated is also the point at which the tumorigenic cells are most difficult to detect.

To facilitate early detection of cancer cells, microfluidic systems that allow isolation and analysis of individual cells in fluid partitions have been developed. The use of microfluidic devices, however, generally requires specialized hardware and technical skill, so microfluidic systems have not been widely adapted for biological applications. Thus, the potential for high-throughput analysis using droplet-based reaction cells remains largely untapped, and traditional cancer diagnostic methods, such as tumor detection and blood cell counts, are still used to detect most cases of cancer. Consequently, each year millions of cases of early-stage cancer continue to go undetected, and the window of opportunity for successfully treating the disease closes for many of those cases.

SUMMARY

The invention provides simple, benchtop devices that generate essentially monodisperse droplets from a bulk liquid. The devices include a shearing mechanism, such as a vortexer, coupled to a vessel holder and an optical system that transmit light to and detects light from liquid in the vessel. When a vessel containing immiscible liquids, such as an aqueous solution and an oil, is placed in the holder, the device applies shearing forces to the liquid. By controlling the duration and amplitude of the shearing force, the device generates an emulsion containing monodisperse droplets. Once near-uniformity in droplet size is achieved, the optical system detects a change in the transmitted light. The device may then cease application of shearing force, notify the user, and/or allow subsequent reactions to be performed.

Because the devices produce essentially monodisperse droplets, they allow isolation of individual targets, such as single cells or molecules, from biological samples. For example, millions of individual targets can be captured in separate fluid partitions in an emulsion contained in a single, macroscopic reaction vessel. Moreover, the droplets can serve as individual reaction cells for processes such as nucleic acid amplification, reverse transcription, and sequencing. Thus, the devices permit large-scale parallel processing of single target cells or molecules in a bulk liquid.

The devices of the invention are superior to prior instruments and systems for generating emulsions of monodisperse droplets. For example, most microfluidic systems require prefabricated microfluidic chips and sophisticated micropneumatic systems. The microfluidic chips are costly to produce and cannot be readily adapted to change production scale. Moreover, the setup and use of microfluidic systems require substantial training. In contrast, the devices of the invention can be used with standard microcentrifuge tubes or assay plates, and their use does not require extensive setup, maintenance, or technical training. Because the devices provided herein include an integrated shearing mechanism, such as motor-driven agitator, and optical system, they also are easier to use than prior vortexers for generating monodisperse emulsions. When immiscible liquids are mixed using other commercially available of vortexers, the extent of emulsification cannot be determined in real time. Insufficient mixing results in droplets that are heterogeneous in size, while excessive mixing exposes the biological contents of the liquid partitions to unnecessary force that may cause damage. The integration of the shearing mechanism and optical system into a single device permits the user to apply only enough shearing force to create monodisperse droplets and to cease application of force once that goal has been achieved.

In aspect, the invention provides devices that include a shearing mechanism for applying shearing energy to a liquid contained in one or more vessels, a holder coupled to the shearing mechanism and configured to secure the vessels, and an optical system that includes a light source positioned to transmit light to the liquid contained in the vessels and a photodetector positioned to sense the transmitted light from the liquid contained in the vessels.

The shearing mechanism may be any device the transmits shearing energy to the liquid. The shearing mechanism may be an agitator, piezoelectric motor, pipettor, shaker, sonicator, or vortexer. The shearing mechanism may be capable of delivering a shearing force within a certain range, e.g., above a first threshold and below a second threshold.

The holder may be any device suitable for holding a vessel. The holder may be or include a clamp, platform, rack, or tray.

The optical system may include multiple light source and multiple photodetectors. Each light source may be positioned to transmit light to the liquid in a different vessel. Each light source may be positioned to transmit light to the liquid in a different well of a vessel. Each photodetector may be positioned to sense the transmitted light from the liquid in a different vessel. Each photodetector may be positioned to sense the transmitted light from the liquid in a different well of a vessel.

The light source may be an argon lamp, deuterium lamp, halogen lamp, laser, light emitting diode (LED) mercury lamp, neon lamp, tungsten lamp, xenon arc lamp, xenon flash lamp, or combination of any of the aforementioned light sources.

The photodetector may be a camera, charge-coupled device (CCD), complementary metal-oxide-semiconductor (CMOS) sensor, diode array, gaseous ionization detector, photodiode, photomultiplier tube, photoresistor, phototransistor, phototube, photovoltaic cell, pinned photodiode, quantum dot photoconductor, or quantum dot photodiode.

The device may include a control system. The control system may be coupled to the shearing mechanism and the optical system. The control system may direct the shearing mechanism to alter the shearing energy applied to the liquid in response to the transmitted light. The control mechanism may increase or decrease the shearing energy. The control system may direct the shearing mechanism to stop applying shearing energy to the liquid when the liquid comprises an emulsion comprising substantially monodisperse droplets.

The device may include a user interface. The user interface may be coupled to the optical system and the shearing mechanism. The user interface may include one or more input sensors that receive input from a user. The input sensor may be a button, dial, keyboard, lever, switch, or touchpad. The user interface may include a display that displays to the user a readout from the optical system.

The device may include one or more vessels. The vessel may be a tube (e.g., a microcentrifuge tube), a strip of tubes (e.g., a strip of 2, 3, 4, 6, 8, 10, 12, or more tubes), or a multiwell plate (e.g., a plate with 2, 4, 6, 8, 12, 24, 48, 96, 192, 384, or more wells).

The device may include an adaptor configured to secure the vessel to the holder. The adaptor may be configured to secure a particular type of vessel, such as any of those described above. The adaptor may be a rack, e.g., a foam rack.

The device may include a temperature regulator that regulates the temperature of the liquid. The temperature regulator may be heating device, a cooling device, or a heating/cooling device.

In another aspect, the invention provides methods for generating an emulsion comprising substantially monodisperse droplets. The methods include contacting one or more vessels containing a liquid with a device that includes a shearing mechanism and a holder configured to secure the vessels and coupled to the shearing mechanism; and applying shearing energy from the shearing mechanism to the liquid, thereby generating an emulsion comprising substantially monodisperse droplets.

The device may include any of the elements described above in relation to devices of the invention.

The method may include transmitting light to the liquid the vessels. The method may include sensing the transmitted light from the liquid in the vessels.

The shearing force may be delivered by vortexing or agitation. The sample may be vortexed or agitated for a defined period. The sample may be vortexed or agitated for about 1 second, about 2 seconds, about 4 seconds, about 6 seconds, about 8 seconds, about 10 seconds, about 15 seconds, about 20 seconds, about 30 seconds, about 45 seconds, about 1 minute, about 2 minutes, about 3 minutes, about 4 minutes, or about 5 minutes. The sample may be vortexed or agitated at a defined speed. The sample may be vortexed or agitated at about 50 rpm, about 100 rpm, about 200 rpm, about 300 rpm, about 400 rpm, about 500 rpm, about 600 rpm, about 700 rpm, about 800 rpm, about 900 rpm, or about 1000 rpm.

The method may include delivering a shearing force within a certain range. The shearing force may be delivered above a first threshold and below a second threshold.

The sample may be vortexed or agitated above about 100 rpm but below about 400 rpm, above about 100 rpm but below about 500 rpm, above about 100 rpm but below about 600 rpm, above about 100 rpm but below about 700 rpm, above about 100 rpm but below about 800 rpm, above about 100 rpm but below about 900 rpm, above about 100 rpm but below about 1000 rpm, above about 200 rpm but below about 400 rpm, above about 200 rpm but below about 500 rpm, above about 200 rpm but below about 600 rpm, above about 200 rpm but below about 700 rpm, above about 200 rpm but below about 800 rpm, above about 200 rpm but below about 900 rpm, above about 200 rpm but below about 1000 rpm, above about 300 rpm but below about 400 rpm, above about 300 rpm but below about 500 rpm, above about 300 rpm but below about 600 rpm, above about 300 rpm but below about 700 rpm, above about 300 rpm but below about 800 rpm, above about 300 rpm but below about 900 rpm, above about 300 rpm but below about 1000 rpm, above about 400 rpm but below about 500 rpm, above about 400 rpm but below about 600 rpm, above about 400 rpm but below about 700 rpm, above about 400 rpm but below about 800 rpm, above about 400 rpm but below about 900 rpm, above about 400 rpm but below about 1000 rpm, above about 500 rpm but below about 600 rpm, above about 500 rpm but below about 700 rpm, above about 500 rpm but below about 800 rpm, above about 500 rpm but below about 900 rpm, above about 500 rpm but below about 1000 rpm, above about 600 rpm but below about 700 rpm, above about 600 rpm but below about 800 rpm, above about 600 rpm but below about 900 rpm, or above about 600 rpm but below about 1000 rpm.

The method may include directing the shearing mechanism to alter the shearing energy applied to the liquid in response to the transmitted light. The method may include directing the shearing mechanism to increase or decrease the shearing energy in response to the transmitted light. The method may include directing the shearing mechanism to stop applying shearing energy to the liquid when the liquid is an emulsion containing substantially monodisperse droplets.

The method include comparing the transmitted light from the liquid in the at least one vessel to a reference. The reference may be transmitted light from a sample that has not been exposed to a shearing force. The reference may be transmitted light from a sample that has monodisperse droplets. The monodisperse droplets may have a defined size or range of sizes.

BRIEF DESCRIPTION OF THE DRAWINGS

FIG. 3 is an illustration of mixing of a sample with a liquid containing partition-templating particles according to a method of the invention.

FIG. 4 is an illustration of addition of a carrier liquid to the mixture according to a method of the invention.

DETAILED DESCRIPTION

The invention provides devices for generating emulsions containing essentially monodisperse droplets and methods of their use. The formation of emulsions containing droplets of uniform size is essential in variety of research and diagnostic applications because it allows individual targets, such as single cells or single molecules, to be captured in separate liquid partitions. By subsequent manipulation of the emulsion, reactions, such as nucleic acid amplification, reverse transcription, and sequencing, can be independently performed on vast numbers of samples simultaneously. Consequently, the devices are useful for detection of aberrant cells or molecules that are present in low quantities, such as tumorigenic cells in an early stage of cancer.

Although the utility of reaction cells that contain individual targets has been recognized for years in molecular biology, prior systems for making emulsions of droplets that contain individual targets are problematic. A predicate to obtaining individualized reaction cells is the production of monodisperse, i.e., uniformly-sized, droplets. Monodisperse droplets can be generated using microfluidic systems, which typically involve controlled injection of two or more liquids into a microfluidic chip having custom-designed fluid channels to permit proper mixing of the liquids. Because the design of a microfluidic must be optimized to produce droplets of a particular size based on the input liquids, microfluidic chips generally cannot be adapted to produce droplets of different sizes for different applications. In addition, because the chips must be prefabricated but typically cannot be reused, they are costly. Finally, the setup and maintenance of microfluidic pumping systems is not trivial and requires a level of trained expertise.

The devices of the invention avoid the pitfalls of microfluidic-based droplet generation. First, the devices permit generation of an emulsion of monodisperse droplets from bulk liquid in simple vessels, such as test tubes or multiwell plates, so they do not require specialized disposable supplies. In addition, because droplet size and contents are determined by the size of particles, discussed in detail below, added to the liquid, the devices can be readily adapted to produce droplets having different properties by altering the content of the input particles. Moreover, the devices are simple to use and do not require extensive cleaning or maintenance between uses.

The invention provides methods of generating monodisperse droplets using devices described herein. A representative workflow for generating monodisperse droplets is described below. The representative workflow is provided for illustrative purposes only and is not intended to limit the scope of the invention. Methods of the invention may include one or more individual steps described in the representative workflow.

Figures 1, 2:
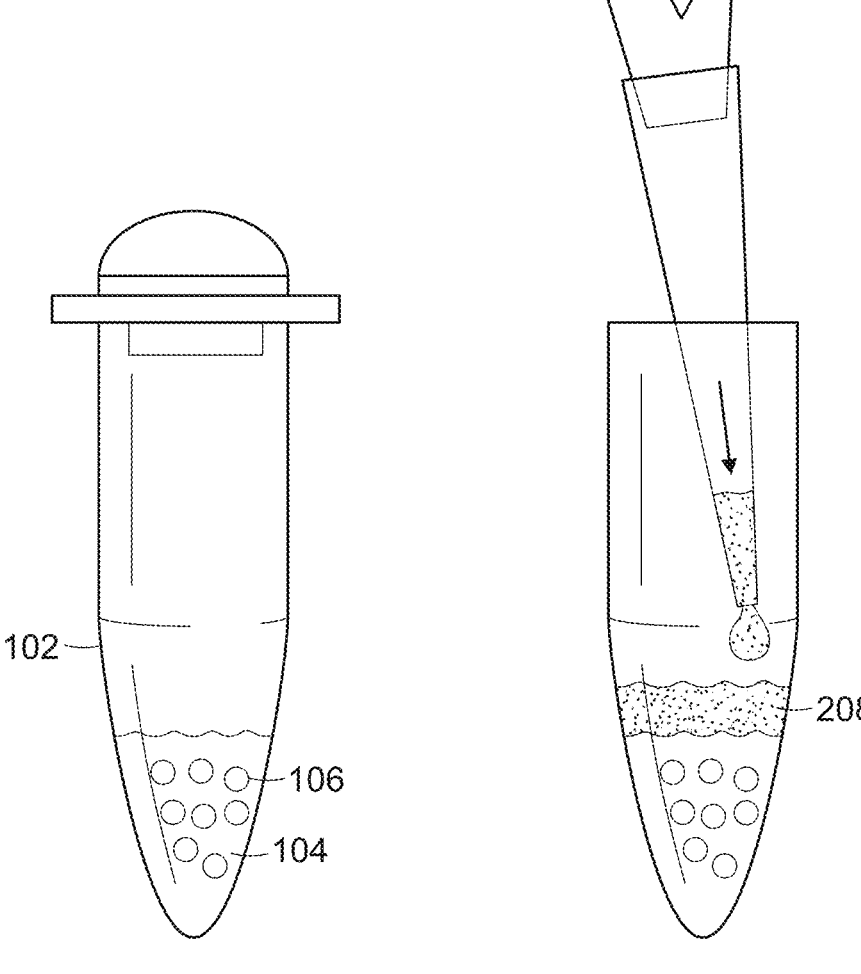
FIG. 1 is an illustration of a vessel containing a liquid with partition-templating particles 106 according to a method of the invention.
FIG. 2 is an illustration of addition of a sample to vessel according to a method of the invention.

FIG. 1 is an illustration of a vessel 102 containing a liquid 104 with partition-templating particles 106 according to a method of the invention. Partition-templating particles 106 are particles of uniform size that promote formation of aqueous droplets in a carrier organic phase, such as an oil. Any type of partition-templating particles 106 may be used, such as those sold under the trade name PIPs (Pre-templated Instant Partitions) by Fluent BioSciences, Watertown, MA. Partition-templating particles 106 may be made from water-soluble polymers, such as polyacrylamide, polyethylene glycol, or agarose. Partition-templating particles 106 are known in the art and described in, for example, Makiko N. Hatori, Particle-Templated Emulsification for Microfluidics-Free Digital Biology, Anal. Chem. 2018, 90, 9813-9820, the content of which are incorporated herein by reference.

The liquid may be any liquid suitable for use with partition-templating particles. The liquid may be an aqueous liquid.

FIG. 2 is an illustration of addition of a sample 208 to vessel according to a method of the invention. The sample may be or include a body fluid from a subject, such as a human. For example and without limitation, the body fluid may be blood, mucus, phlegm, plasma, saliva, semen, serum, stool, sweat, synovial fluid, tears, or urine. The sample 208 contains multiple targets. The targets may be any molecule or structure of interest. For example and without limitation, the targets may be or include cells, viruses, molecules, macromolecules, nucleic acids (e.g., RNA, DNA, RNA/DNA hybrids, etc.), proteins, peptides, polypeptides, carbohydrates, hormones, or any combination thereof. The sample 208 may be added to the vessel manually or robotically.

FIG. 3 is an illustration of mixing of a sample with a liquid containing partition-templating particles according to a method of the invention. The mixing may be performed manually or robotically. For example and without limitation, the mixing may be done by vortexing, pipetting, shaking, or any other type of movement of the vessel. Mixing produces a mixture 310 that contains targets and partition-templating particles.

FIG. 4 is an illustration of addition of a carrier liquid 412 to the mixture according to a method of the invention. The carrier liquid 412 may any liquid that is immiscible with the liquid that makes up the bulk phase of the mixture. The carrier liquid 412 may be or include an organic liquid, such as an oil. For example and without limitation, the carrier oil may be a fluorocarbon oil, a silicone oil, a hydrocarbon oil, or any combination thereof. The carrier liquid 412 may have density greater than or less than the density of the liquid that makes up the bulk phase of the mixture. The carrier liquid may contain one or more surfactants. For example and without limitation, the surfactant may be a non-ionic detergent, PEG-PFPE amphiphilic block copolymer surfactant, octylphenoxypolyethoxyethanol, octylphenol ethoxylate, or polysorbate 20. The carrier liquid 412 may contain one or more reducing agents. For example and without limitation, the reducing agent may be dithiothreitol or beta mercaptoethanol. The carrier liquid 412 may be added manually or robotically.

Figure 5:
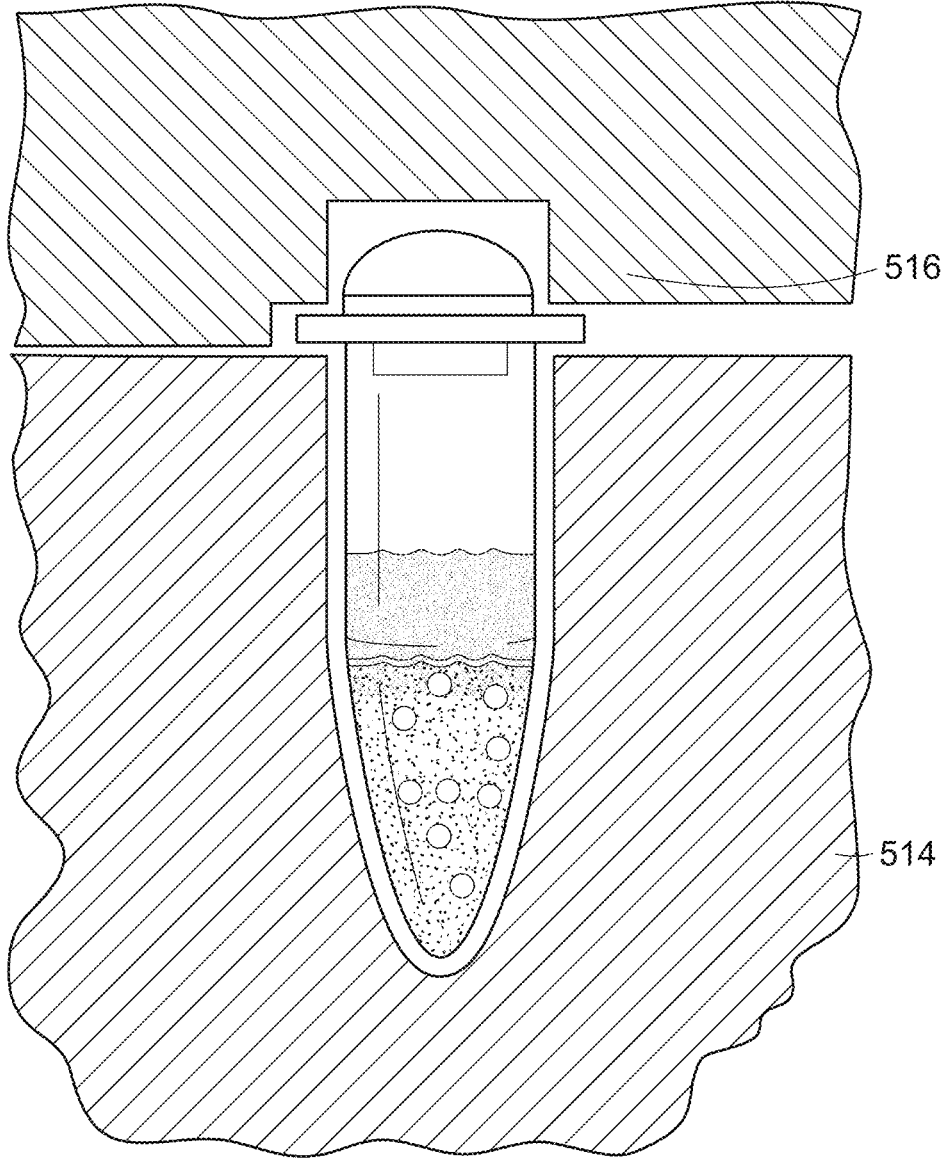
FIG. 5 is an illustration of a vessel secured within a holder of a device according to a method of the invention.

FIG. 5 is an illustration of a vessel 502 secured within a holder 514 of a device according to a method of the invention. Prior to operation of the device, the vessel contains two liquid phases: the carrier liquid and the mixture containing the partition-templating particles and targets. The vessel is supported by a holder 514. For example and without limitation, the holder may be a platform, rack, or tray. The holder may include a clamp 516. The clamp 516 may integral with the platform, rack, or tray, or it may be separate from the platform, rack, or tray.

Once the vessel is secured with the holder of the device, an optical measurement may be taken for each sample prior to formation of a monodisperse emulsion. The optical measure may be taken by emitting light from a light source into the sample and sensing light transmitted from the sample using a photodetector. The optical measurement taken before shearing force is applied to the sample serves as a baseline measurement the sample. The baseline measurement may be used to normalize measurements for variability among different samples, different vessels, different assay runs, and the like.

A shearing force is then applied to the sample to generate an emulsion containing droplets of the liquid of the mixture, which is typically aqueous, within the carrier liquid, which is typically organic. Any type of shearing force may be applied to the sample. The shearing force may be applied by one or more of mechanical, sonic, or electrical means. For example and without limitation, the force may be applied mechanically by agitating, pipetting, rotating, shaking, spinning, or vortexing the sample. For example and without limitation, the force may be applied sonically by sonication or ultrasound. For example and without limitation, the force may be applied electrically via a piezoelectric effect.

Optimal generation of monodisperse droplets may be achieved by applying a shearing force within a certain range. For example, when the shearing force is inadequate, large droplets that contain multiple partition-templating particles may not be broken into single-particle droplets. On the other hand, excessive shearing force may damage the particles and/or the targets to be captured by the droplets. Thus, the shearing force applied may be above a lower threshold but below an upper threshold.

In certain embodiments, a shearing force is applied by vortexing or agitating the sample. The sample may be vortexed or agitated for a defined period. For example and without limitation, the sample may be vortexed or agitated for about 1 second, about 2 seconds, about 4 seconds, about 6 seconds, about 8 seconds, about 10 seconds, about 15 seconds, about 20 seconds, about 30 seconds, about 45 seconds, about 1 minute, about 2 minutes, about 3 minutes, about 4 minutes, or about 5 minutes. The sample may be vortexed or agitated at a defined speed. For example and without limitation, the sample may be vortexed or agitated at about 50 rpm, about 100 rpm, about 200 rpm, about 300 rpm, about 400 rpm, about 500 rpm, about 600 rpm, about 700 rpm, about 800 rpm, about 900 rpm, or about 1000 rpm. For example and without limitation, the sample may be vortexed or agitated above about 100 rpm but below about 400 rpm, above about 100 rpm but below about 500 rpm, above about 100 rpm but below about 600 rpm, above about 100 rpm but below about 700 rpm, above about 100 rpm but below about 800 rpm, above about 100 rpm but below about 900 rpm, above about 100 rpm but below about 1000 rpm, above about 200 rpm but below about 400 rpm, above about 200 rpm but below about 500 rpm, above about 200 rpm but below about 600 rpm, above about 200 rpm but below about 700 rpm, above about 200 rpm but below about 800 rpm, above about 200 rpm but below about 900 rpm, above about 200 rpm but below about 1000 rpm, above about 300 rpm but below about 400 rpm, above about 300 rpm but below about 500 rpm, above about 300 rpm but below about 600 rpm, above about 300 rpm but below about 700 rpm, above about 300 rpm but below about 800 rpm, above about 300 rpm but below about 900 rpm, above about 300 rpm but below about 1000 rpm, above about 400 rpm but below about 500 rpm, above about 400 rpm but below about 600 rpm, above about 400 rpm but below about 700 rpm, above about 400 rpm but below about 800 rpm, above about 400 rpm but below about 900 rpm, above about 400 rpm but below about 1000 rpm, above about 500 rpm but below about 600 rpm, above about 500 rpm but below about 700 rpm, above about 500 rpm but below about 800 rpm, above about 500 rpm but below about 900 rpm, above about 500 rpm but below about 1000 rpm, above about 600 rpm but below about 700 rpm, above about 600 rpm but below about 800 rpm, above about 600 rpm but below about 900 rpm, or above about 600 rpm but below about 1000 rpm.

Following the application of a shearing force to the sample, another optical measurement may be taken. The post-shearing optical measurement provides an indication of the extent of partitioning throughout the sample and the level of heterogeneity of droplets within the emulsion.

Figure 6:
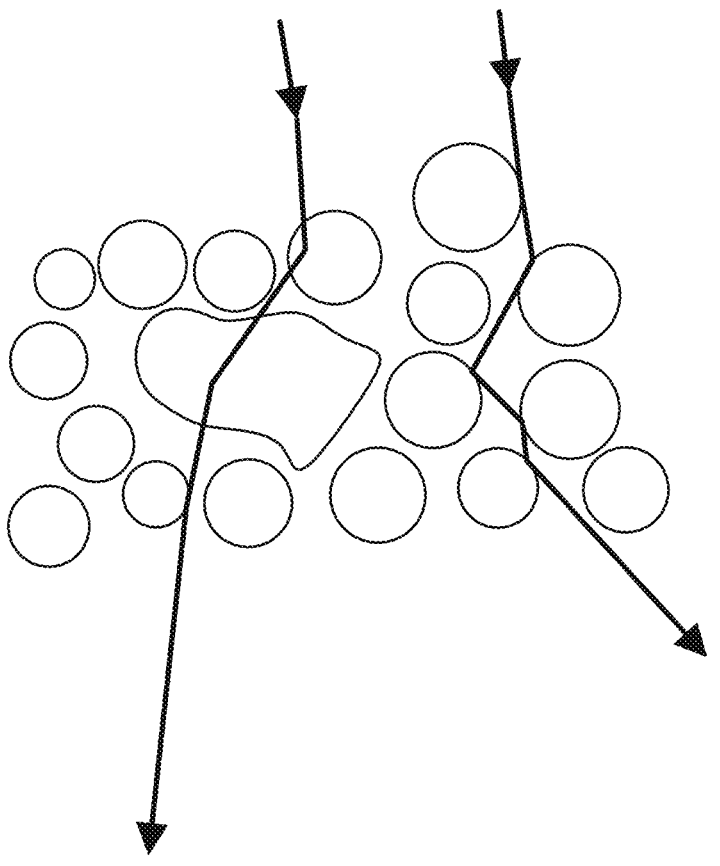
FIG. 6 is a schematic of light transmitted through an emulsion according to a method of the invention.

FIG. 6 is a schematic of light transmitted through an emulsion according to a method of the invention. The light beam on the left passes through droplets that are heterogeneous in size, including one large droplet or "raft", whereas the light beam on the left passes through droplets that are small and homogeneous in size. Because the light beam on the right passes through more interfaces between the two immiscible liquids, it experiences greater deflection and attenuation as it passes through the sample than does the light beam on the left. Consequently, less light is transmitted through a sample with small, monodisperse droplets than through a sample with heterogeneous droplets.

Figure 7:
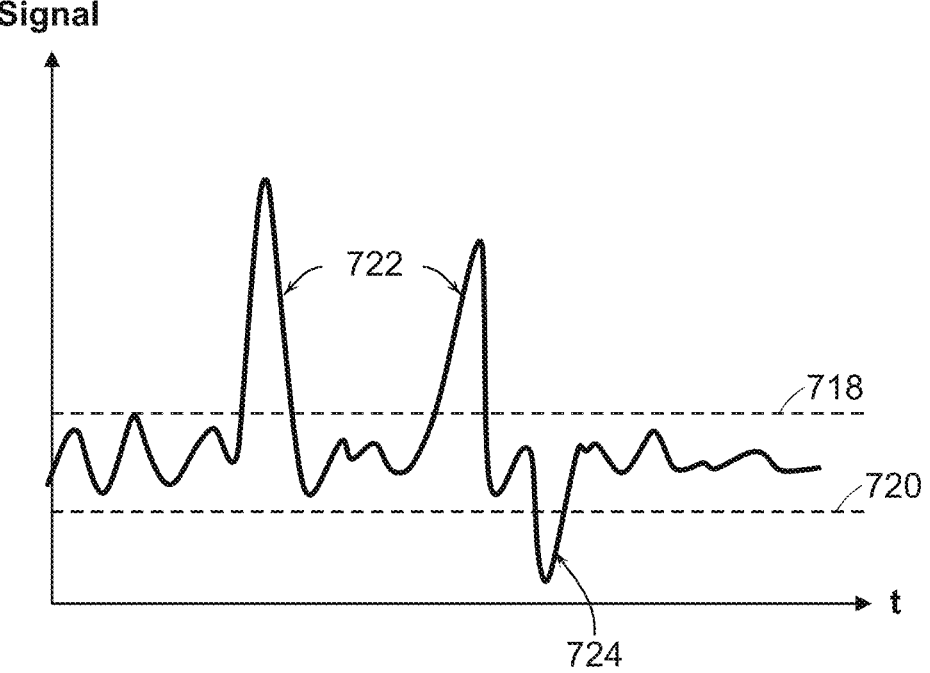
FIG. 7 is a graph of the signal intensity of a light transmitted through an emulsion during a method of the invention.

FIG. 7 is a graph of the signal intensity of a light transmitted through an emulsion during a method of the invention. The dashed lines indicate the maximum 718 and minimum 720 signal intensities expected from a sample containing droplets that are substantially uniform in size. The uniformity in droplet size results from each droplet containing a single partition-templating particle, as the partition-templating particles are essentially uniform in size. Peaks 722 of high signal intensity indicate passage of light through rafts, or large droplets that contain multiple partition-templating particles. The nadir 724 of low signal intensity indicates passage of light through "satellite" droplets than contain no partition-templating particles.

The transmitted light signal may be compared to a reference to determine whether additional shearing force should be applied to the sample to achieve monodisperse droplets. The reference may be transmitted light from a sample, e.g., the same sample or a different sample, prior to exposure of the sample to a shearing force. The reference may be transmitted light from a sample that has monodisperse droplets. The monodisperse droplets may have a defined size or range of sizes.

If the first post-shearing optical measurement indicates that the emulsion contains droplets that are heterogeneous in size, the shearing and measurement steps may be repeated as many times as necessary to achieve monodisperse droplets. The decision on whether to repeat the shearing and measuring steps may rely on human input. Alternatively or additionally, the decision may be made automatically by an algorithm. The algorithm may include pre-defined maximum and minimum signal intensities. Alternatively or additionally, the maximum and minimum signal intensities may be determined via a machine-learning process.

The use of partition-templating particles to generate monodisperse droplets allows individual targets to be captured. By adjusting the concentration of targets in the starting sample in combination with the formation of droplets of uniform size, an emulsion can be produced in which all or nearly all droplets contain either zero or one target. See Makiko N. Hatori, Particle-Templated Emulsification for Microfluidics-Free Digital Biology, Anal. Chem. 2018, 90, 9813-9820, the content of which are incorporated herein by reference. Therefore, each droplet can serve as a reaction cell for performing a reaction on a single target.

Method of the invention may include performing reactions in the monodisperse droplets formed by one or more of the steps described above. For example and without limitation, the methods may include one or more of cell lysis, nucleic acid amplification, reverse transcription, or sequencing.

Performing reactions in droplets formed according to one or more of the steps described above may include adjusting the temperature of the emulsions. For example, the methods may include heating and/or cooling the samples.

Figure 8:
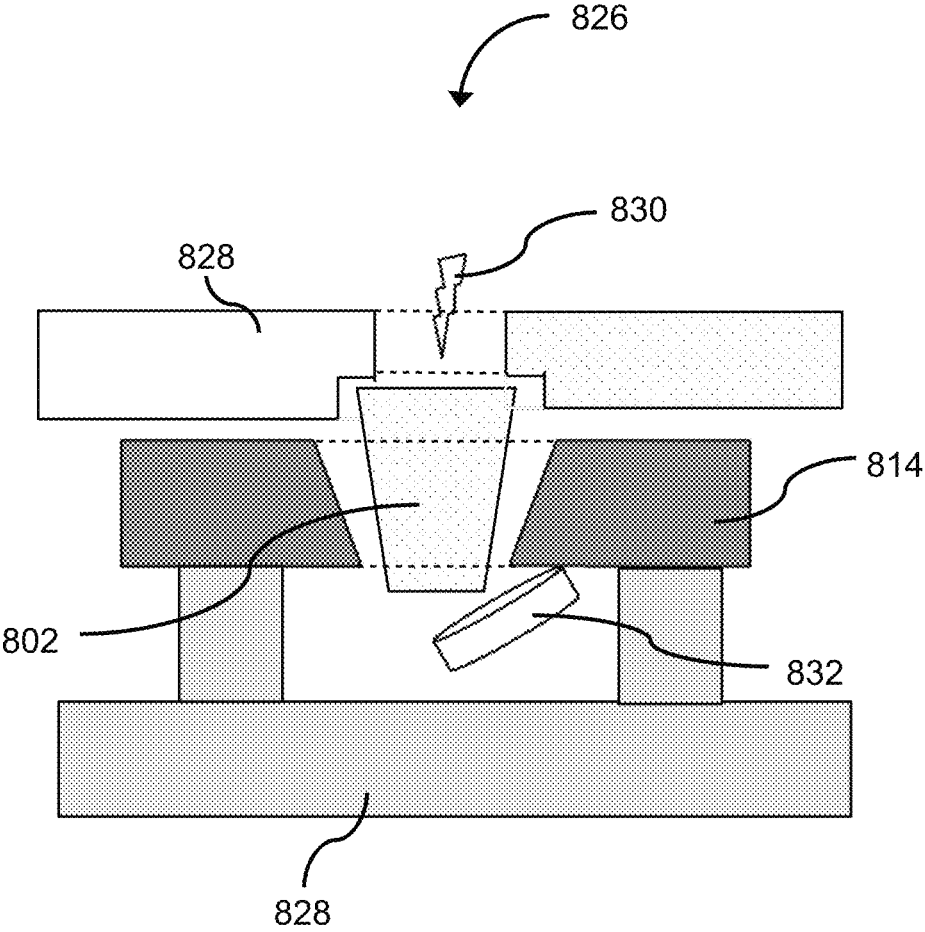
FIG. 8 is a schematic of a device according to an embodiment of the invention. The device 826 includes a shearing mechanism coupled to a holder.

FIG. 8 is a schematic of a device 826 according to an embodiment of the invention. The device 826 includes a shearing mechanism 828 coupled to a holder 814. The holder 814 is configured to hold a vessel 802. The holder 814 may be or include a platform, rack, or tray. The holder 814 may also include or be coupled with a clamp 828 that helps to secure the vessel 802 when shearing force is applied. The device 826 may include an adaptor configured to secure the vessel 802 to the holder. The adaptor may be configured to secure a particular type of vessel, such as any of those described above. The adaptor may be a rack, e.g., a foam rack.

The device 826 also includes an optical system that includes a light source 830 and a photodetector 832. The light source 830 is positioned to transmit light to the liquid contained in the vessel 802. The photodetector 832 is position to sense the transmitted light from the liquid contained in the vessel 802.

Figure 9:
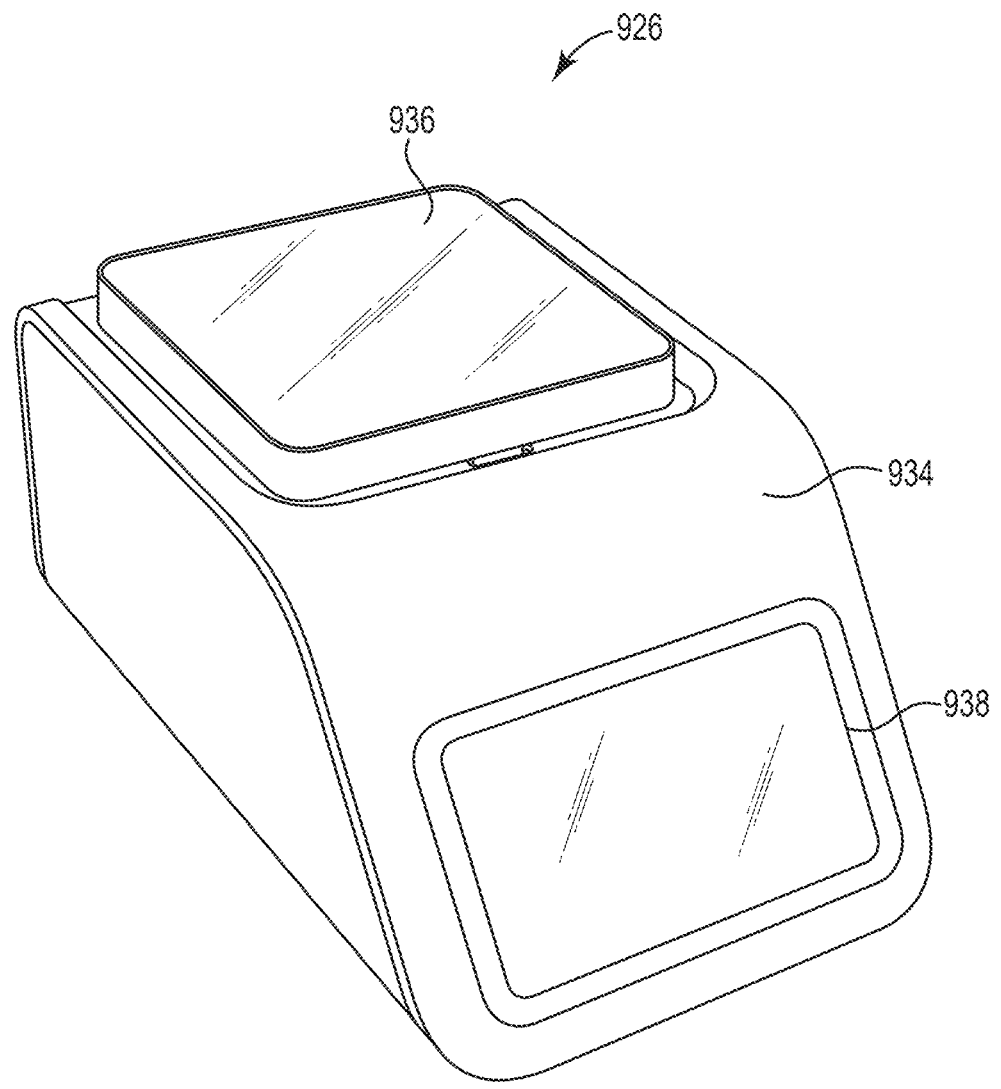
FIG. 9 is in image of a device according to an embodiment of the invention.

FIG. 9 is in image of a device 926 according to an embodiment of the invention. The device 926 includes a housing 934 and lid 936 that enclose the vessel while device 926 is in use. The device 926 also includes a user interface 938 that provides output to and/or receives input from a user.

Figure 10:
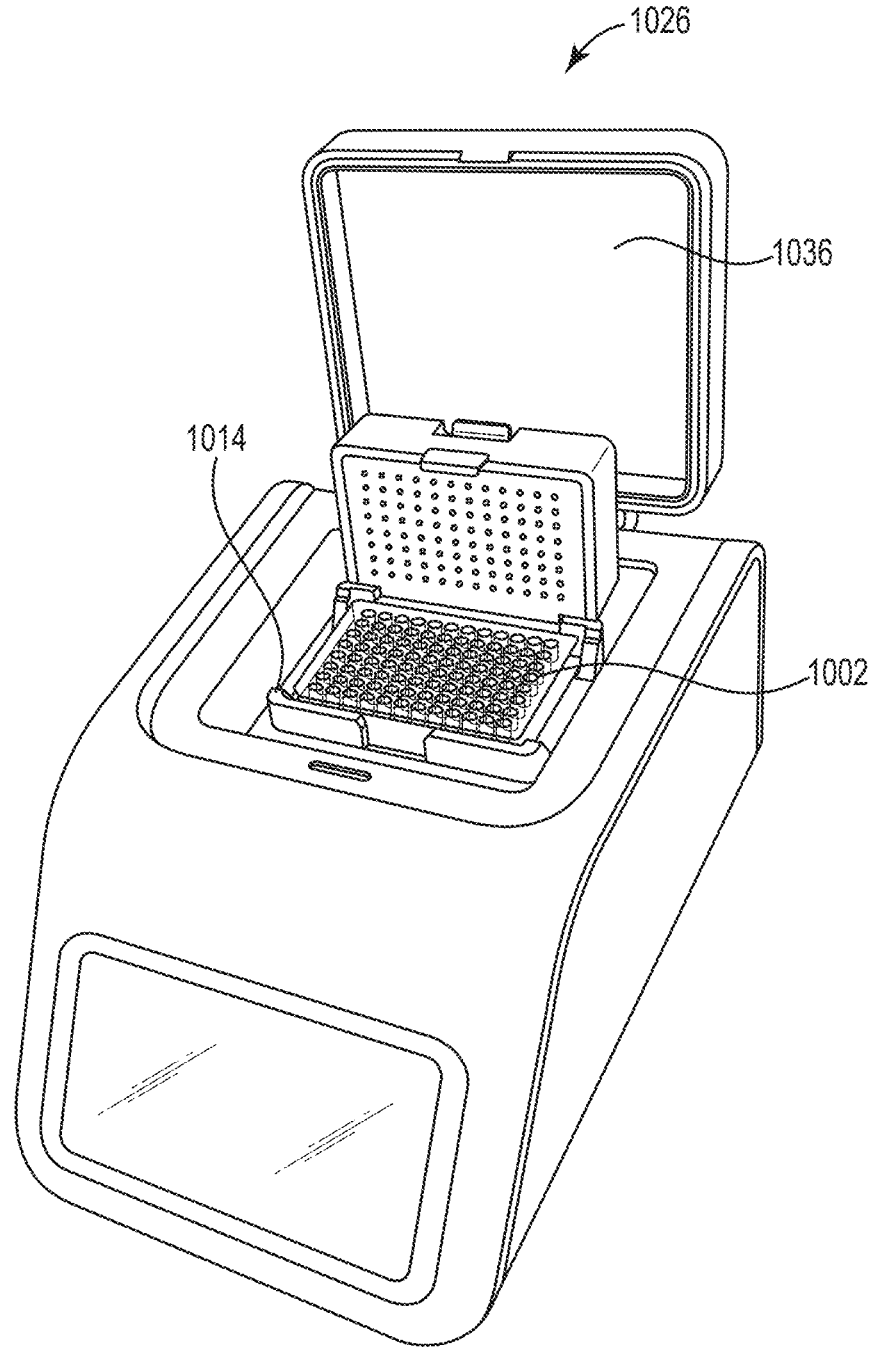
FIG. 10 is in image of a device according to an embodiment of the invention.

FIG. 10 is in image of a device 1026 according to an embodiment of the invention. The device 1026 includes a lid 1036, which opens to allow the user to insert a vessel 1002 into the holder 1014.

The shearing mechanism may be any device capable of applying a shearing force to the liquid in the vessel. In some embodiments, the shearing force is applied by moving the vessel, such as by spinning, rotating, shaking, or rocking the vessel. In such embodiments, the shearing mechanism may be or include an agitator, shaker, or vortexer. In some embodiments, the shearing force is applied by moving the liquid in the vessel directly, such as by pipetting or stirring the liquid. In such embodiments, the shearing mechanism may be or include a pipettor or mixer. In some embodiments, the shearing force is applied through an electrical force. In such embodiments, the shearing mechanism may be or include a piezoelectric motor. In some embodiments, the shearing force is applied through sound waves. In such embodiments, the shearing mechanism may be or include a sonicator or ultrasonic device. The shearing force may be applied by a combination of means, and the shearing mechanism may be or include any combination of the aforementioned devices.

The vessel may be any container suitable for holding liquid. For example and without limitation, the vessel may be a tube or a well in a multiwell plate. The vessel may be or include a set of tubes physically connected to each other. For example, the vessel may be or include a strip of 2, 3, 4, 6, 8, 10, 12, or more tubes. The vessel may be or include a well in plate with 2, 4, 6, 8, 12, 24, 48, 96, 192, 384, or more wells.

Figure 11:
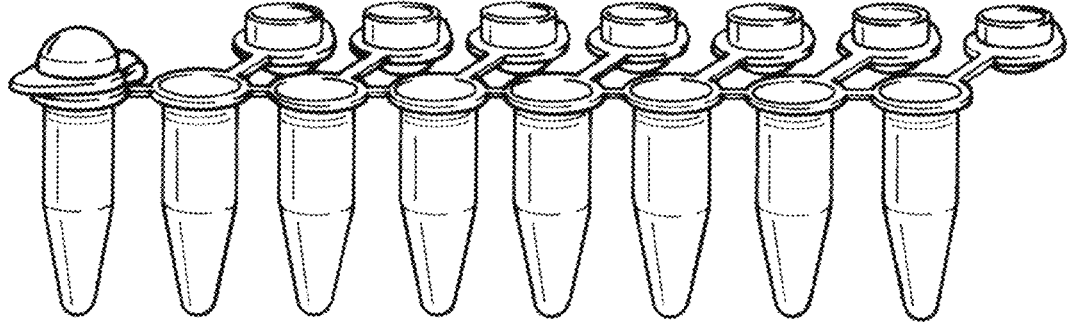
FIG. 11 is an illustration of a strip of microcentrifuge tubes suitable for use in embodiments of the invention.

FIG. 11 is an illustration of a strip of 8 microcentrifuge tubes suitable for use in embodiments of the invention.

Any light source suitable for transmission of light into a liquid may be used for the device. For example and without limitation, the light source may be or include an argon lamp, deuterium lamp, halogen lamp, laser, light emitting diode (LED) mercury lamp, neon lamp, tungsten lamp, xenon arc lamp, xenon flash lamp, or combination of any of the aforementioned light sources.

Similarly, any photodetector suitable for detection of light transmitted from a liquid may be used. For example and without limitation, the photodetector may be or include a camera, charge-coupled device (CCD), complementary metal-oxide-semiconductor (CMOS) sensor, diode array, gaseous ionization detector, photodiode, photomultiplier tube, photoresistor, phototransistor, phototube, photovoltaic cell, pinned photodiode, quantum dot photoconductor, or quantum dot photodiode.

The holder and optical system may be movable relative to each other so that light can be transmitted to and sensed from multiple vessels or multiple chambers within a vessel. For example, in some embodiments the light source and photodetector is fixed within the device, and the holder is movable in one, two, or three dimensions to adjust the position of the liquid sample in relation to the light source and photodetector. In other embodiments, the holder is fixed within the device, and the light source and photodetector are movable in one, two, or three dimensions to adjust the position of the liquid sample in relation to the light source and photodetector. In other embodiments, both the holder and optical system are movable in one, two, or three dimensions to adjust the position of the liquid sample in relation to the light source and photodetector.

In some embodiments, the device includes a control system coupled to the shearing mechanism and the optical system. The control system directs the shearing mechanism to alter the shearing energy applied to the liquid in response to the transmitted light. The control mechanism may increase or decrease the shearing energy. The control system may direct the shearing mechanism to stop applying shearing energy to the liquid when the liquid comprises an emulsion comprising substantially monodisperse droplets.

In some embodiments, the device includes a user interface that allows interaction between the user and the device. The user interface may provide output about the sample to the user. For example and without limitation, the user interface may provide information on the optical measurement that indicates whether the sample is contains monodisperse droplets or on the duration and/or intensity of shearing forces applied. The user interface may include a display. The user interface may allow the user to provide input, such as information on the desired size or range of sizes of monodispersed droplets to be obtained by shearing or on the duration and/or intensity of shearing forces applied. The user interface may include a button, dial, keyboard, lever, switch, or touchpad.

The optical system may include multiple light sources and photodetectors. For example, when a multitube vessel or multiwell vessel is used, the optical system may have a separate light source and photodetector for each tube or well. Alternatively or additionally, the optical system may have a separate light source and photodetector for each row of tubes or wells. In some embodiments, one light source is used in conjunction with multiple photodetectors to allow multiple measurements to be taken from a single liquid sample.

The optical system may include the light source and photodetector in a variety of spatial arrangements relative to the vessel, holder, and liquid sample. Some exemplary configurations for optical systems in devices of the invention are described below.

Figure 12:
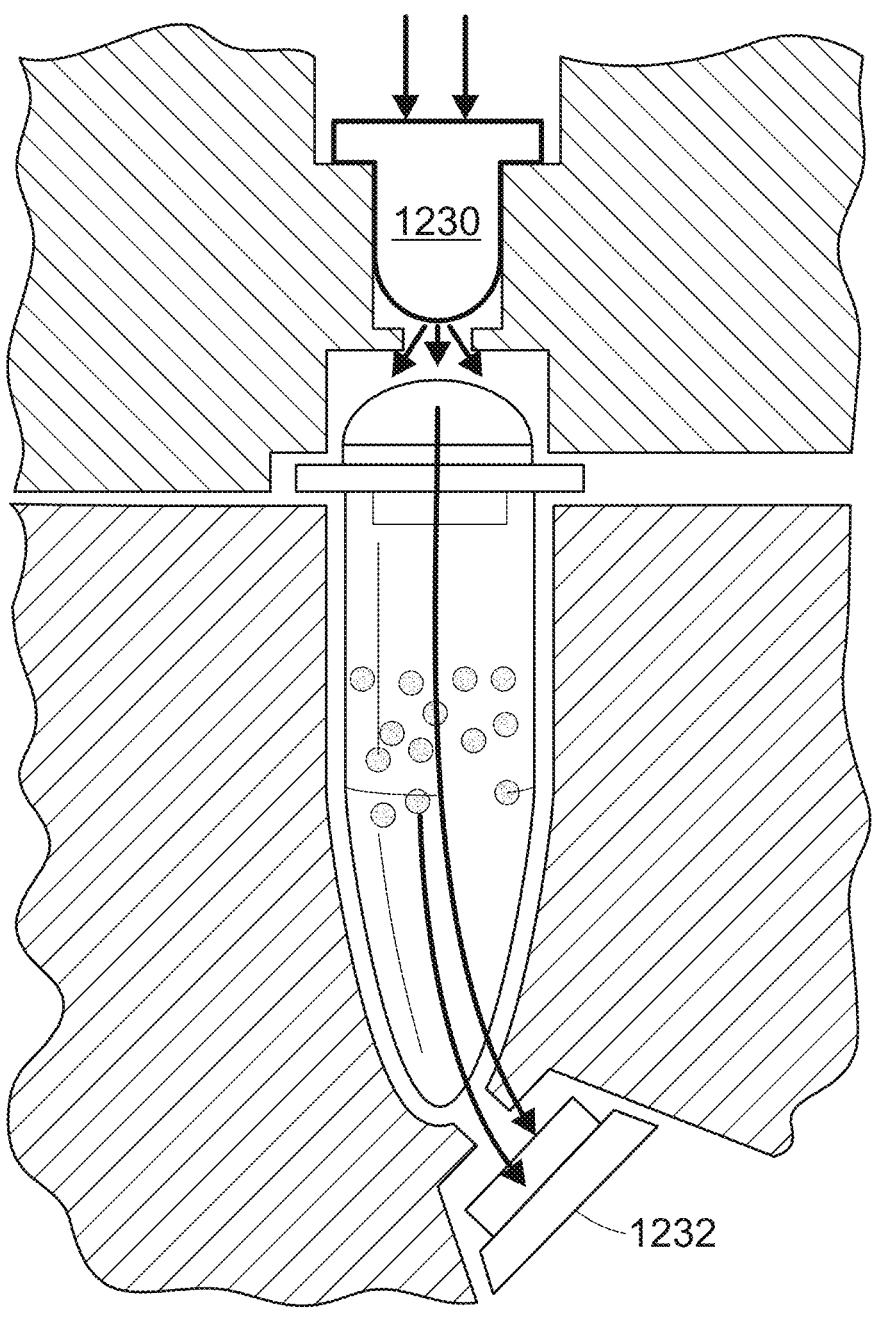
FIG. 12 is an illustration of a vessel secured in a holder in a device according to an embodiment of the invention.

FIG. 12 is an illustration of a vessel secured in a holder in a device according to an embodiment of the invention. The device includes a light source 1230 positioned above the vessel and a photodetector 1232 positioned below the vessel and offset at an angle.

Figure 13:
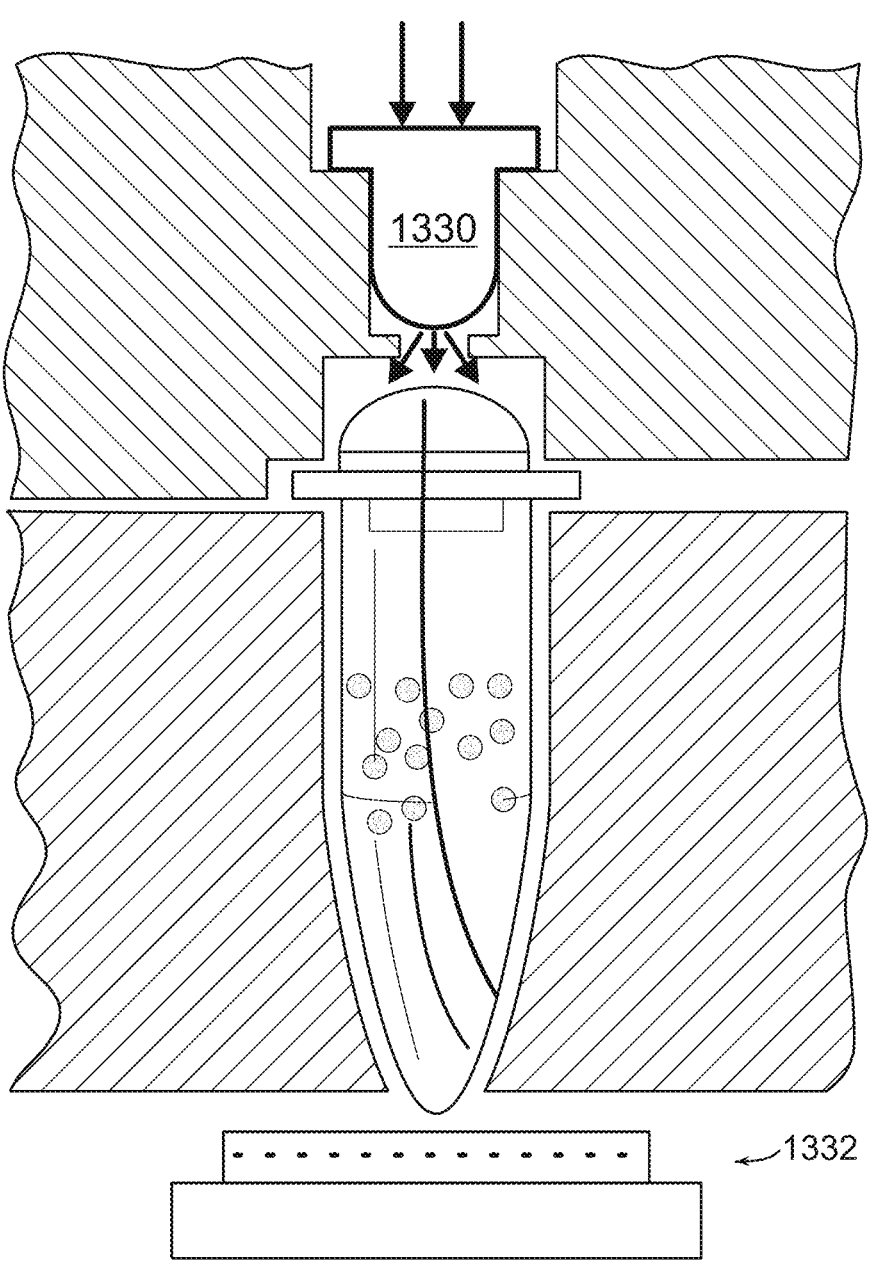
FIG. 13 is an illustration of a vessel secured in a holder in a device according to an embodiment of the invention.

FIG. 13 is an illustration of a vessel secured in a holder in a device according to an embodiment of the invention. The device includes a light source 1330 positioned above the vessel and a photodetector 1332 positioned below the vessel. The photodetector 1332 includes a multiple sensors positioned in a linear or two-dimensional array.

Figure 14:
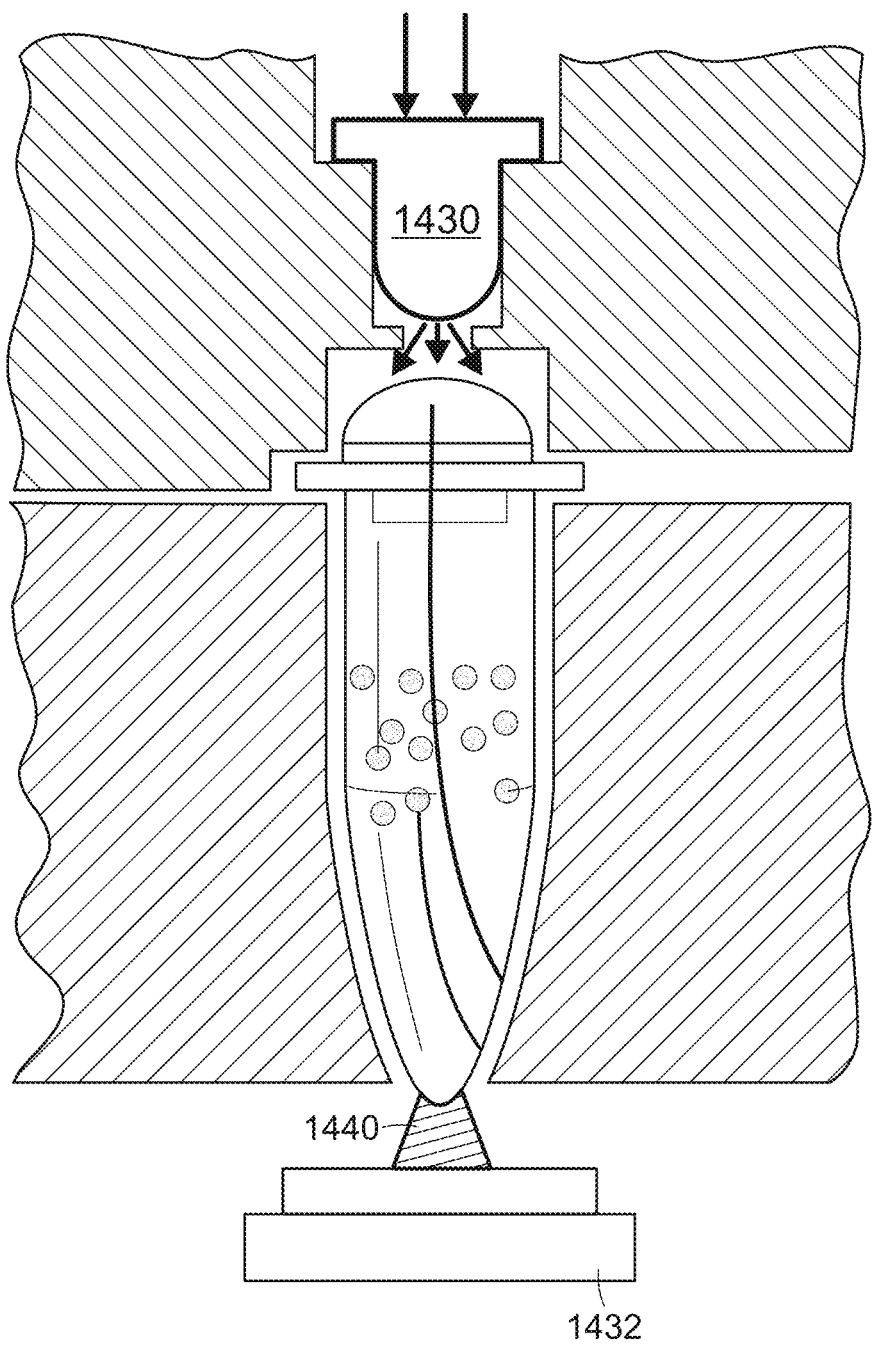
FIG. 14 is an illustration of a vessel secured in a holder in a device according to an embodiment of the invention.

FIG. 14 is an illustration of a vessel secured in a holder in a device according to an embodiment of the invention. The device includes a light source 1430 positioned above the vessel and a photodetector 1432 positioned below the vessel. The photodetector 1432 includes a single large sensor that has a light block 1440 in the center to prevent detection of pass-through light.

Figure 15:
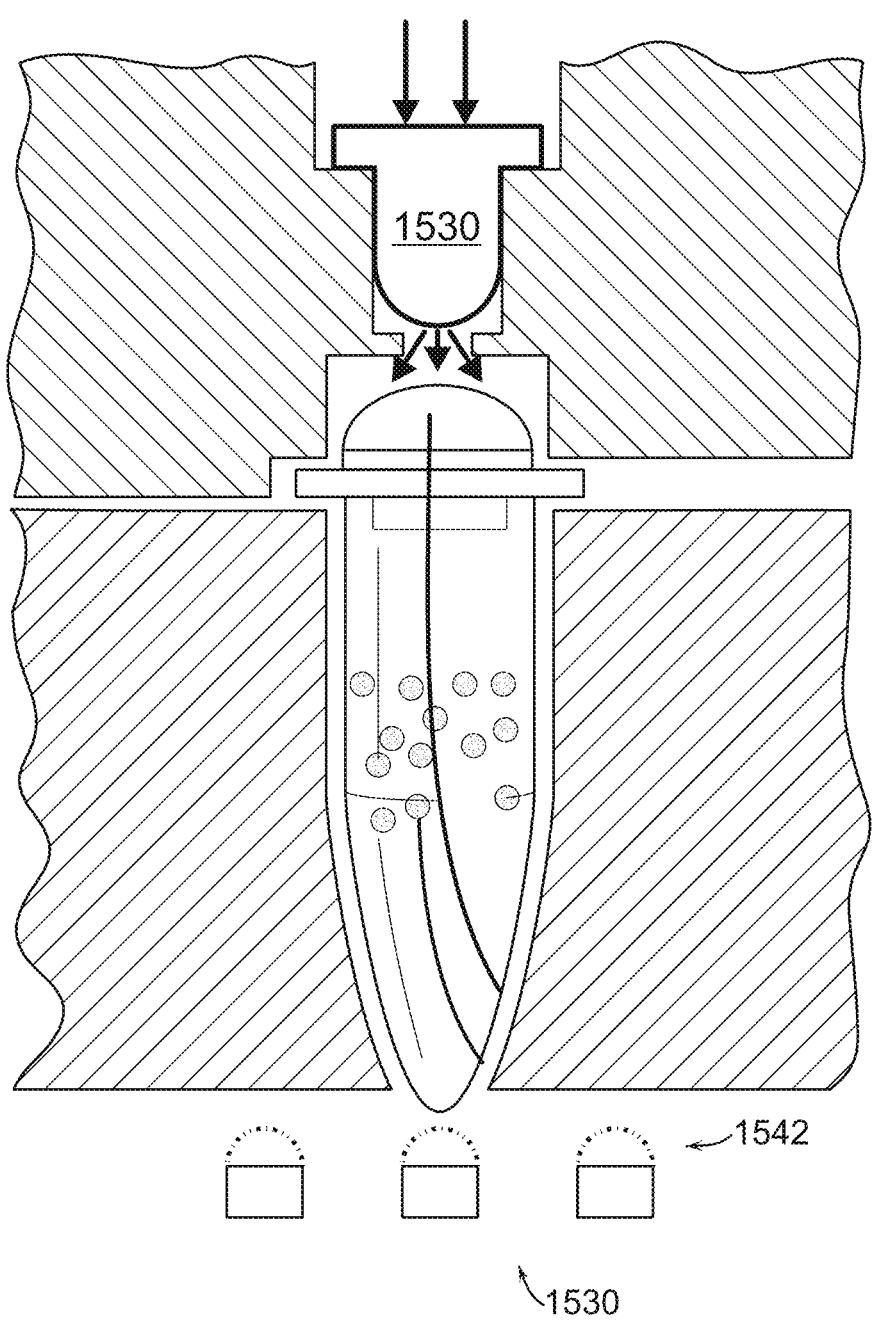
FIG. 15 is an illustration of a vessel secured in a holder in a device according to an embodiment of the invention.

FIG. 15 is an illustration of a vessel secured in a holder in a device according to an embodiment of the invention. The device includes a light source 1530 positioned above the vessel and a photodetector 1532 positioned below the vessel. The photodetector 1532 includes a multiple sensors, each of which is covered by a lens 1542.

Figure 16:
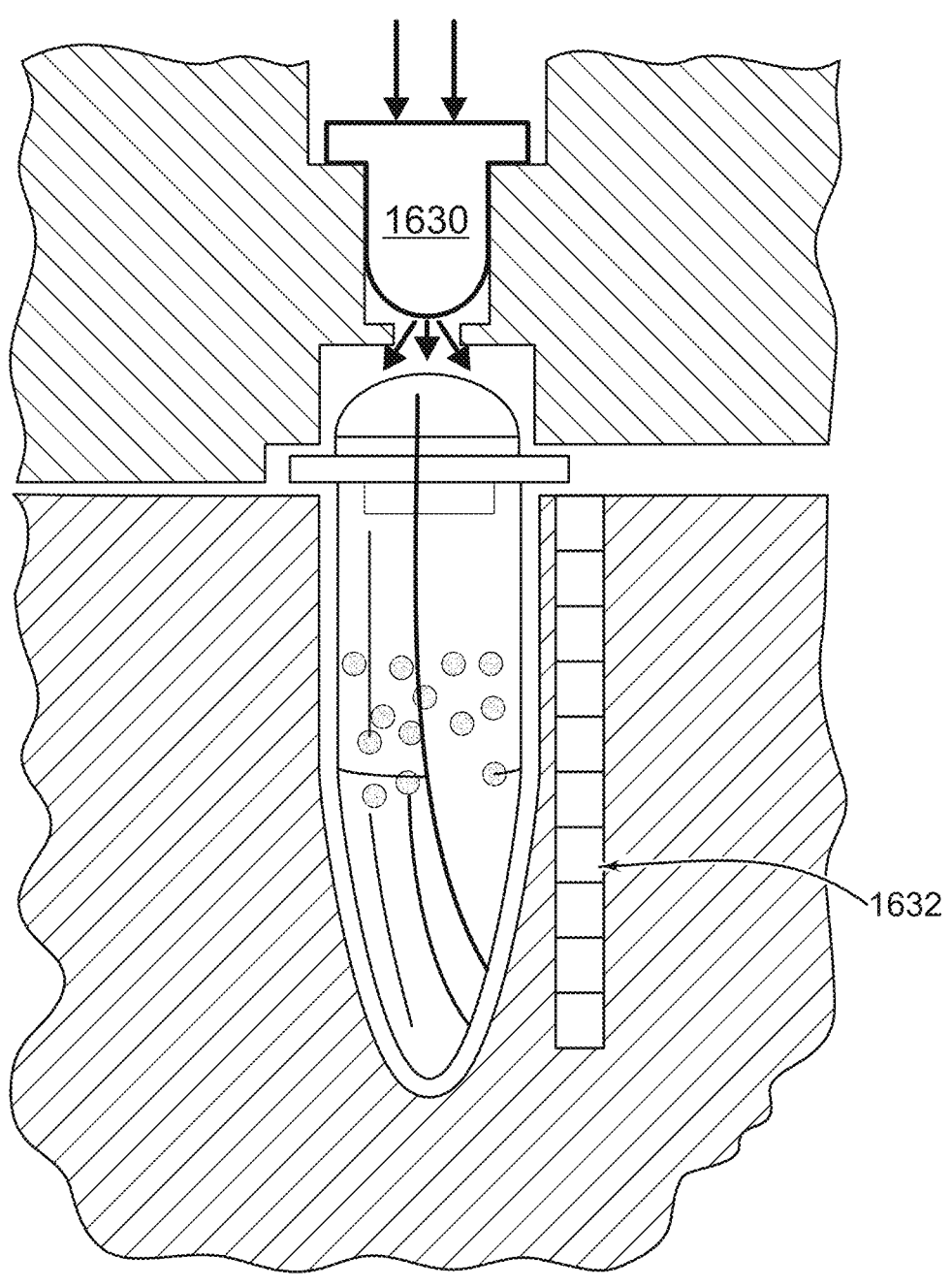
FIG. 16 is an illustration of a vessel secured in a holder in a device according to an embodiment of the invention.

FIG. 16 is an illustration of a vessel secured in a holder in a device according to an embodiment of the invention. The device includes a light source 1630 positioned above the vessel and a photodetector 1632 positioned to one side of the vessel. The photodetector 1632 includes a multiple sensors positioned in a linear or two-dimensional array.

Figure 17:
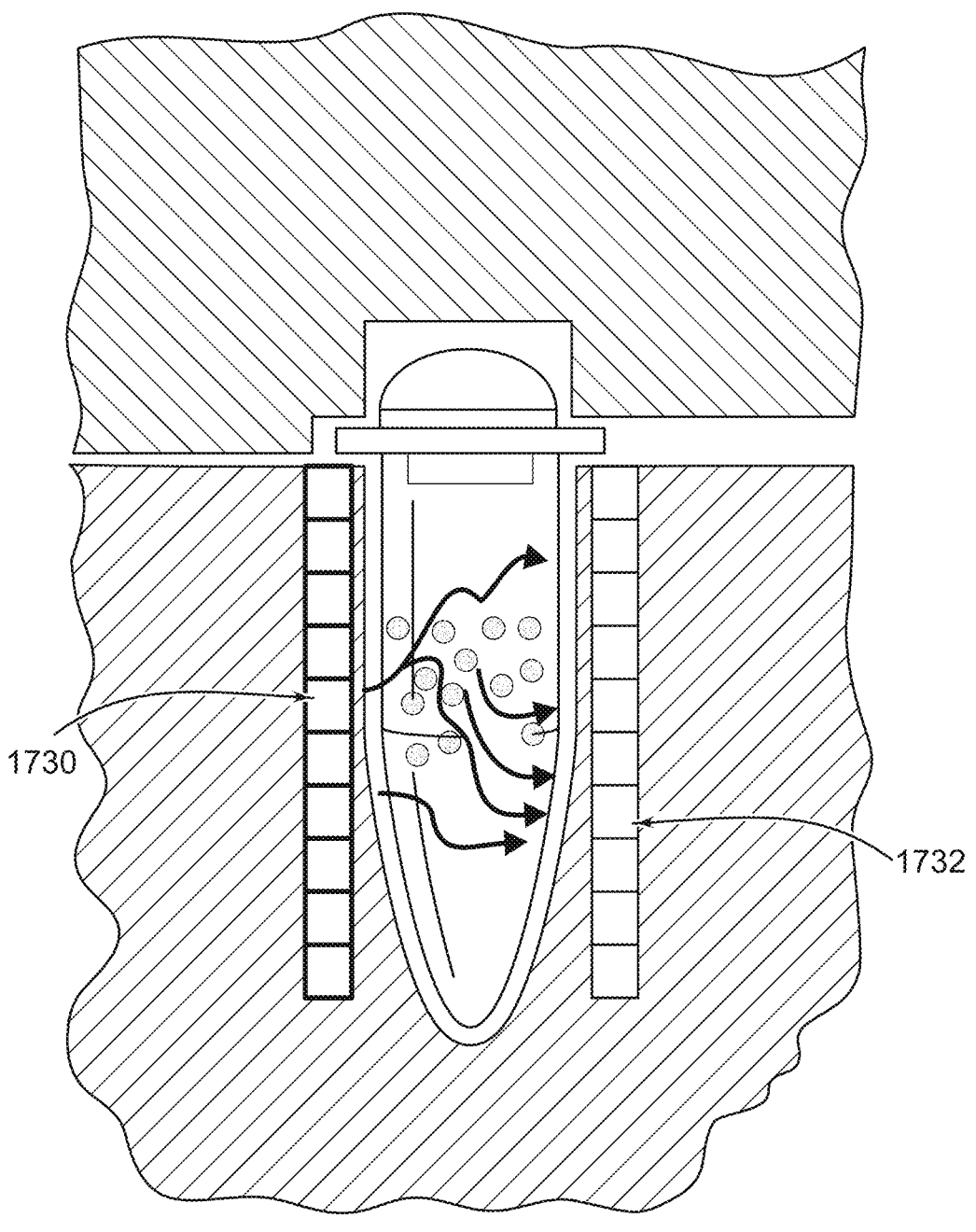
FIG. 17 is an illustration of a vessel secured in a holder in a device according to an embodiment of the invention.

FIG. 17 is an illustration of a vessel secured in a holder in a device according to an embodiment of the invention. The device includes a light source 1730 positioned to one side of the vessel and a photodetector 1732 positioned to the opposite side of the vessel. The photodetector 1732 includes a multiple sensors positioned in a linear or two-dimensional array.

Figure 18:
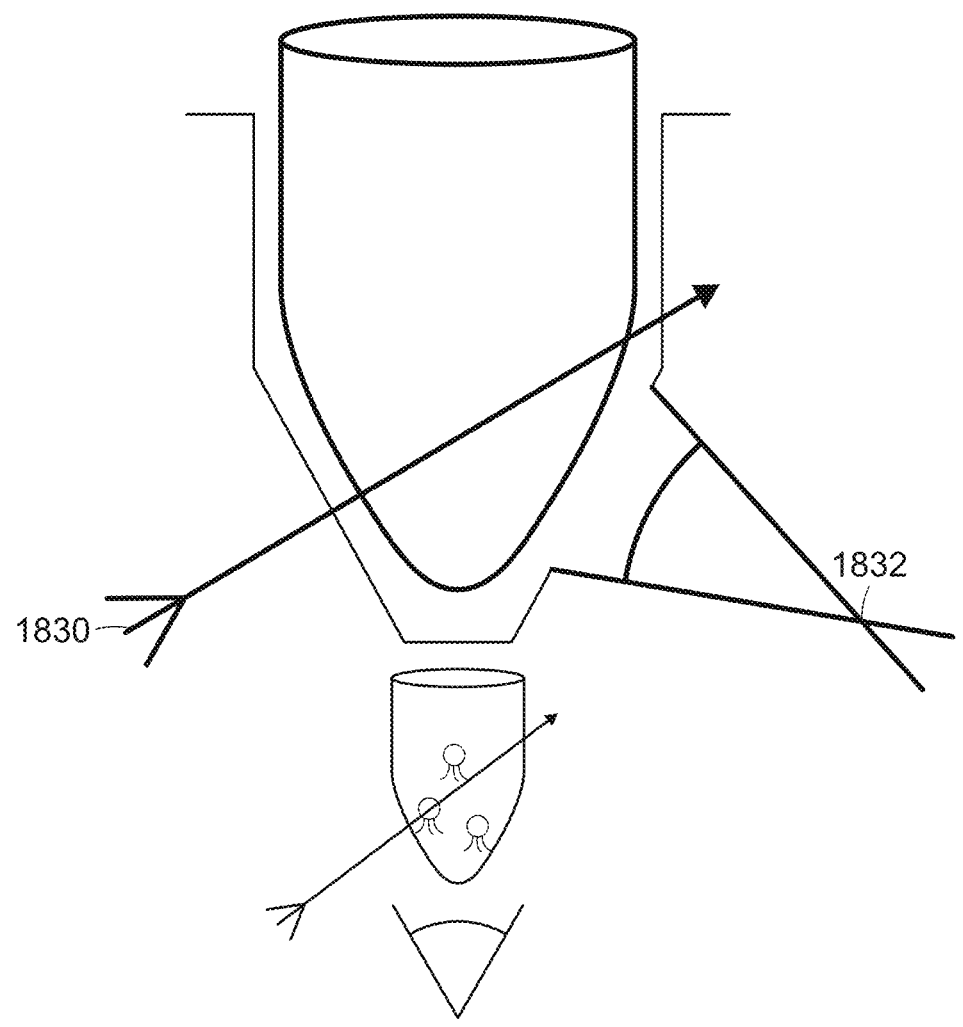
FIG. 18 is an illustration of a vessel secured in a holder in a device according to an embodiment of the invention.

FIG. 18 is an illustration of a vessel secured in a holder in a device according to an embodiment of the invention. The device includes a light source 1830 positioned below and to one side of the vessel at angle orthogonal to a conical surface of the vessel and a photodetector 1832 positioned below and to the opposite side of the vessel at angle orthogonal to a conical surface of the vessel. Due to the conical shape of the bottom of the tube, the light source 1830 and photodetector 1832 do not face each other, so only scattered light is detected by the photodetector 1832.

Devices of the invention may include additional elements that allow reactions to be performed in the monodisperse droplets. For example, the device may include a temperature regulator that regulates the temperature of the liquid. The temperature regulator may be heating device, a cooling device, or a heating/cooling device.

EXAMPLES

Example 1

The ability to determine whether an emulsion contains monodisperse droplets using an optical system was analyzed. A test fixture including a light source above the vessel and a photodetector comprising a single sensor positioned below and at an angle to the vessel, similar to device described in FIG. 12, was used. Samples were vortexed to create emulsions. The photodetector was able to distinguish between emulsion states before and after vortexing.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A device comprising:
   a shearing mechanism for applying shearing energy to thereby generate an emulsion to a liquid contained in at least one vessel;
   a holder coupled to the shearing mechanism and configured to secure the at least one vessel;
   an optical system comprising:
      a light source positioned to transmit light to the liquid contained in the at least one vessel, and
      a photodetector positioned to sense the transmitted light from the liquid contained in the at least one vessel, wherein the holder and optical system are movable relative to each other to adjust the position of the at least one vessel in relation to the light source and the photodetector; and
   a control system coupled to the shearing mechanism and the optical system,
   wherein the control system directs the shearing mechanism to alter the shearing energy applied to the liquid in response to the transmitted light and directs the shearing mechanism to stop applying shearing energy when the emulsion comprises substantially monodisperse droplets, and
   wherein the control system directs the shearing mechanism to stop applying shearing energy in response to the photodetector sensing the transmitted light from the liquid contained in the at least one vessel within pre-defined maximum and minimum intensities of the sensed transmitted light.

2. The device of claim 1, wherein the shearing mechanism is selected from the group consisting of an agitator, piezo-electric motor, pipettor, shaker, sonicator, and vortexer.

3. The device of claim 2, wherein the shearing mechanism is a vortexer.

4. The device of claim 1, wherein the holder comprises a clamp.

5. The device of claim 1, wherein the light source is selected from the group consisting of a laser and a light emitting diode (LED).

6. The device of claim 1, wherein the photodetector is selected from the group consisting of a camera, charge-coupled device (CCD), complementary metal-oxide-semiconductor (CMOS) sensor, diode array, gaseous ionization detector, photodiode, photomultiplier tube, photoresistor, phototransistor, phototube, photovoltaic cell, pinned photodiode, quantum dot photoconductor, and quantum dot photodiode.

7. The device of claim 1, further comprising a user interface coupled to the optical system and the shearing mechanism, the user interface comprising:

at least one input sensor that receives input from a user; and a display that displays to the user a readout from the optical system.

8. The device of claim 1, further comprising an adaptor configured to secure the at least one vessel to the holder.

9. The device of claim 1, further comprising a temperature regulator that regulates temperature of the liquid.

10. The device of claim 1, further comprising the at least one vessel.

11. The device of claim 10, wherein the device comprises a plurality of vessels.

12. The device of claim 1, wherein:

the at least one vessel comprises a plurality of wells that contain the liquid; and the optical system comprises:

a plurality of light sources, each light source positioned to transmit light to a liquid contained in one of the plurality of wells, and a plurality of photodetectors, each photodetector positioned to sense the transmitted light from the liquid contained in one of the plurality of wells.

13. The device of claim 1, wherein the holder is movable in at least one dimension to adjust the position of the at least one vessel in relation to the light source and the photodetector; the light source and the photodetector are movable in at least one dimension to adjust the position of the at least one vessel in relation to the light source and the photodetector; or both.

14. A method for generating an emulsion comprising substantially monodisperse droplets, the method comprising:

contacting at least one vessel containing a liquid with a device comprising:

a shearing mechanism, a holder configured to secure the at least one vessel and coupled to the shearing mechanism, and an optical system comprising a light source and a photodetector, wherein the holder and optical system are movable relative to each other to adjust the position of the at least one vessel in relation to the light source and the photodetector;

applying shearing energy from the shearing mechanism to the liquid, thereby generating an emulsion comprising substantially monodisperse droplets;

adjusting the position of the holder relative to the optical system;

transmitting light from the light source to the liquid in the at least one vessel;

sensing, with the photodetector, the transmitted light from the liquid in the at least one vessel; and directing the shearing mechanism to alter the shearing energy applied to the liquid in response to the photodetector sensing the transmitted light from the liquid contained in the at least one vessel within pre-defined maximum and minimum intensities of the sensed transmitted light.

15. The method of claim 14, wherein the directing step comprises directing the shearing mechanism to stop applying shearing energy to the liquid when the liquid comprises an emulsion comprising substantially monodisperse droplets.

16. The method of claim 14, further comprising:

comparing the transmitted light from the liquid in the at least one vessel to a reference.

17. The method of claim 14, wherein the holder is movable in at least one dimension to adjust the position of the at least one vessel in relation to the light source and the photodetector; the light source and the photodetector are movable in at least one dimension to adjust the position of the at least one vessel in relation to the light source and the photodetector; or both.

* * * * *